(12) United States Patent
Nelson et al.

(10) Patent No.: US 8,206,732 B2
(45) Date of Patent: Jun. 26, 2012

(54) PYRITHIONE BIOCIDES ENHANCED BY SILVER, COPPER, OR ZINC IONS

(75) Inventors: John D. Nelson, Bethlehem, CT (US); Thomas J. Palys, Berlin, CT (US); Jon R. Geiger, West Hartford, CT (US)

(73) Assignee: Arch Chemicals, Inc., Norwalk, CT (US)

( * ) Notice: Subject to any disclaimer, the term of this patent is extended or adjusted under 35 U.S.C. 154(b) by 0 days.

(21) Appl. No.: 12/288,557

(22) Filed: Oct. 21, 2008

(65) Prior Publication Data

US 2009/0047851 A1   Feb. 19, 2009

Related U.S. Application Data

(62) Division of application No. 09/599,371, filed on Jun. 22, 2000, now Pat. No. 7,455,851.

(60) Provisional application No. 60/141,195, filed on Jun. 25, 1999.

(51) Int. Cl.
| | |
|---|---|
| A01N 25/34 | (2006.01) |
| A01N 25/00 | (2006.01) |
| A01N 25/32 | (2006.01) |
| A01N 59/16 | (2006.01) |
| A01N 59/30 | (2006.01) |

(52) U.S. Cl. ........ 424/405; 424/404; 424/406; 424/618; 424/630

(58) Field of Classification Search .......... 424/404–406, 424/618, 630
See application file for complete search history.

(56) References Cited

U.S. PATENT DOCUMENTS

| | | | |
|---|---|---|---|
| 2,786,847 A | 3/1957 | Cislak | |
| 2,809,971 A | 10/1957 | Bernstein et al. | |
| 3,236,733 A | 2/1966 | Karsten et al. | |
| 3,589,999 A | 6/1971 | McRae et al. | |
| 3,590,035 A | 6/1971 | Damico | |
| 3,773,770 A | 11/1973 | Damico | |
| 3,852,441 A | 12/1974 | Kooistra, Jr. | |
| 4,055,655 A | 10/1977 | Maurer et al. | |
| 4,161,526 A | 7/1979 | Gorman | |
| 4,235,873 A | 11/1980 | Packman | |
| 4,370,325 A | 1/1983 | Packman | |
| 4,608,183 A | 8/1986 | Rossmoore | |
| 4,654,213 A | 3/1987 | Ramirez et al. | |
| 4,666,616 A | 5/1987 | Rossmoore | |
| 5,227,156 A | 7/1993 | Wiese | |
| 5,462,589 A | 10/1995 | Nicholas | |
| 5,518,774 A | 5/1996 | Kappock et al. | |
| 5,562,995 A | 10/1996 | Kappock et al. | |
| 5,614,538 A | 3/1997 | Nelson | |
| 5,854,266 A | 12/1998 | Nelson | |
| 5,874,476 A | 2/1999 | Hsu et al. | |
| 5,880,076 A | 3/1999 | Vermeer | |
| 5,883,154 A | 3/1999 | Kappock et al. | |
| 6,017,562 A | 1/2000 | Kaufman et al. | |

FOREIGN PATENT DOCUMENTS

| | | |
|---|---|---|
| EP | 0 077 630 | 4/1983 |
| GB | 761171 | 11/1956 |
| GB | 2 230 190 A | 10/1990 |
| JP | HEI 6-134227 | 5/1994 |
| JP | 6-256689 | 9/1994 |
| JP | HEI 7-118103 | 5/1995 |
| KR | 1997-010124 | 3/1997 |
| WO | WO 99/21568 | 5/1999 |

OTHER PUBLICATIONS

Bennett et al., "*The Effects of Metals Upon the Inhibitory Activities of Cutting Fluid Preservatives*", International Biodeterioration Bulletin ISSN 0020-6164 19(1), Spring 1982.
Akiyama et al., "*Effects of zinc oxide on the attachment of Staphylococcus aureus strains*", Journal of Dermatological Science, 17 (1998), pp. 67-74.
"*Aspects of the mode of action of pyrithione against Klebsiella pneumoniae*", by M. M. Khattar and W. G. Salt, Journal of Antimicrobial Chemotherapy 1993, 5(S1), pp. 175-177.

*Primary Examiner* — Lynda Salvatore
(74) *Attorney, Agent, or Firm* — Gianna Julian-Arnold; Saul Ewing LLP

(57) ABSTRACT

The present invention is directed to an antimicrobial composition, comprising pyrithione or a pyrithione complex; and a zinc or copper or silver source selected from the group consisting of zinc or copper or silver salts, oxides, hydroxides, sulfates, chlorides, metals, and combinations thereof; wherein the weight ratio of the zinc or copper or silver source to the pyrithione or the pyrithione complex is in the range from about 1:300 to about 50:1, and wherein the antimicrobial composition has an enhanced biocidal effect against a variety of free-living microorganisms or biofilms. Also disclosed is a method of inhibiting the growth of free-living microorganisms or biofilm utilizing the above antimicrobial composition, as well as use of such antimicrobial compositions in various products including fuels, fluids, lubricants, coatings, adhesives, sealants, elastomers, soaps, cosmetics, plastic or woven or non-woven fibers, pharmaceuticals, and as preservatives for the above products.

11 Claims, 1 Drawing Sheet

PYRITHIONE BIOCIDES ENHANCED BY SILVER, COPPER, OR ZINC IONS

This application is a Divisional of U.S. patent application Ser. No. 09/599,371 filed Jun. 22, 2000, now U.S. Patent No. 7,455,851, which claims the benefit of U.S. Provisional Application 60/141,195 filed Jun. 25, 1999. All the aforementioned U.S. Applications are incorporated by reference herein in their entireties

BACKGROUND OF THE INVENTION

1. Field of the Invention

The present invention is directed to pyrithione biocides, and more particularly to a biocidal composition displaying an enhanced biocidal effect, comprising an antimicrobially effective combination of pyrithione, pyrithione salt, or pyrithione adduct, and metal ion such as a zinc or copper or silver source such as copper and/or zinc and/or silver metal, oxide, hydroxide, or salt thereof.

2. Brief Description of the Related Art

Polyvalent metal salts of pyrithione (also known as 1-hydroxy-2-pyridinethione; 2-pyridinethiol-1-oxide; 2-pyridinethione; 2-mercaptopyridine-N-oxide; pyridinethione; and pyridinethione-N-oxide) are known to be effective biocidal agents, and are widely used as fungicides and bacteriocides in paints and metalworking fluids. Pyrithiones are also used as fungicides and bacteriocides in personal care products such as anti-dandruff shampoos. The polyvalent metal salts of pyrithione are only sparingly soluble in water and include magnesium pyrithione, barium pyrithione, bismuth pyrithione, strontium pyrithione, copper pyrithione, zinc pyrithione, cadmium pyrithione, and zirconium pyrithione. The most widely used divalent pyrithione salts are zinc pyrithione and copper pyrithione.

Zinc and copper pyrithione are useful as antimicrobial agents active against gram-positive and negative bacteria, fungi, and yeasts. Zinc pyrithione is used as an antidandruff component in shampoos, while technical suspensions of zinc pyrithione and/or copper pyrithione are used as preservatives in paints and polymers. Synthesis of polyvalent pyrithione salts are described in U.S. Pat. No. 2,809,971 to Berstein et al. Other patents disclosing similar compounds and processes for making them include U.S. Pat. Nos. 2,786,847; 3,589, 999; 3,590,035; 3,773,770.

While pyrithione biocides have proven useful for a wide range of applications as outlined above, the utility of these compounds is limited to the control of select species and strains of fungi and bacteria. Further, while higher concentrations of pyrithione or its salts have been observed to control the growth of a wider range of organisms, the useful amount of pyrithione or its salts that can be added to a commercial product is limited by efficacy and economic considerations, and, to a lesser extent, environmental and toxicological concerns.

Copper compounds, such as copper sulfate and cuprous oxide, have been used widely as fungicides, antifoulants, and algaecides in a large range of applications including paints, swimming pool water, and wood products such as structural members for buildings or boats. Similarly, inorganic salts of zinc such as zinc chloride zinc sulfate and zinc oxide, have been employed as bacteriostatic and/or fungistatic compounds in a large variety of products including paints, coatings, and antiseptics. However, while copper salts and zinc salts are less toxic than pyrithione or its salts, these compounds do not possess the high biocidal efficacy that is desired in many commercial applications.

Certain combinations of pyrithione and zinc are known in the art. Illustratively, U.S. Pat. Nos. 5,854,266 and 5,883,154 disclose an aqueous antimicrobial composition protected against discoloration attributable to the presence of ferric ion or cupric ion therein, wherein the composition comprises pyrithione and a discoloration-inhibiting amount (between 0.001% to 10%) of a zinc compound selected from the group consisting of zinc salts of organic acids, zinc salts of inorganic acids, zinc hydroxide, zinc oxide, and combinations thereof. In another illustration, U.S. Pat. No. 4,161,526 discloses a white to cream yellow pyrithione salt or dipyrithione for application to skin or hair containing 0.01% to 1% of the zinc salt of an organic or inorganic acid, zinc hydroxide, zinc oxide, or combinations thereof. However, this patent does not describe any advantageous effect between pyrithione and the zinc salt.

While bacteria and fungi have presented microbial contamination problems for many years, biofilms have recently been appreciated as a significant new source of microbial contamination. Biofilms are generally characterized as aggregates of cells adhered to one another or to surfaces by an extracellular layer of slime. Biofilms are commonly found as contaminants in metalworking fluids because these fluids contain good carbon sources for growth of the organisms that are found in biofilms. However, high concentrations of biofilms in metalworking fluid result in rapid deterioration of the fluid, and can cause equipment problems and failure.

The growth of biofilms on surfaces can also enhance the rates of corrosion of metal surfaces and degradation of paints, surface coatings and the construction materials underlying these coatings. On ship hulls, the presence of biofilms can lead to increased drag and may encourage colonization by larger invertebrate biofouling organisms. Biofilms are often responsible for both internal and cutaneous infections. The increased resistance of biofilms to antimicrobial treatments often make biofilm-related infections more difficult to treat. Medical devices, such as cardiac implants and catheters, and medical instruments, such as dialysis machines and dental waterlines also become contaminated by biofilms and can spread infection.

While previous efforts have been made to control the growth and proliferation of biofilms, these efforts have met with only limited success. Research has indicated that biofilm cells are much more resistant to disinfection than free-living cells, due in large part to the extracellular slime layer which acts as a protective coating. Moreover, strategies to control microbial contamination heretofore were typically developed in the laboratory against free-living organisms, and little or no attention was given towards determining the effectiveness of antimicrobial agents against biofilm. Unfortunately, the resistant biofilms are generally not affected by previously employed antimicrobials. If not removed or destroyed, biofilms can cause a multitude of problems in functioning fluid applications, such as corrosion, clogging, slime build up on surfaces, foul odors, fluid instability, machine down-time, and the like.

Additional representative patents and publications showing the state of the art in the microbial disinfection area are as follows:

U.S. Pat. No. 5,462,589 discloses a composition of made from a copper salt and sodium pyrithione, and chelates thereof. The mixture is applied sequentially, fixing the preservative in the wood.

U.S. Pat. No. 4,654,213 discloses an antimicrobial composition in which a water-soluble salt of zinc enhances the activity of the $MgSO_4$ adduct of 2,2'-dithiopyridine-1,1'-dioxide (MDS).

U.S. Pat. No. 4,370,325 discloses a composition containing 2,2'-dithiopyridine-1,1'-dioxide or one of its metal salt adducts, including $MgSO_4$ (MDS) and Zn salts, for treating eye and ear irritation and inflammation.

U.S. Pat. No. 4,235,873 discloses a deodorant composition containing 2,2'-dithiopyridine-1,1'-dioxide or one of its metal salt adducts, including $MgSO_4$ (MDS) and Zn salts.

British Patent GB 2 230 190 A discloses a preservative composition containing an isothiazolone and the $ZnCl_2$ adduct of 2,2'-dithiopyridine-1,1'-dioxide. However, this patent does not describe any advantageous effect between pyrithione and the zinc salt.

Japanese patent application 6-134227 discloses an antibacterial filter incorporating ZnO or ZnO and zinc pyrithione. However, this patent does not describe any advantageous effect between pyrithione and the zinc salt.

Japanese patent application 7-118103 discloses an antimicrobial composition for coating stainless steel washing machine drums to prevent fouling of inner surfaces wherein ZnO is used as a carrier in a ZPT thermoplastic resin coating. However, this patent does not describe any advantageous effect between pyrithione and the zinc salt.

Japanese patent application 06256689 discloses antifungal coatings composed of zeolites impregnated with heavy metals, preferably silver, and either a benzimidazole or a metal salt of 2-pyridiylthio-1-oxide, preferably, zinc.

ZnO may enhance the activities of hinokitiol, and certain antibiotics against artificial biofilms of *S. aureus* (Effects of Zinc Oxide on the Attachment of *Staphylococcus aureus* Strains, H. Akiyama, et al., J. Dermatol. Science 17: 67-74, 1998)

The presence of 0.2% metallic copper or 0.2% metallic zinc was found to decrease the biocidal activity sodium pyrithione in 12 different metalworking fluids (E. O. Bennet et al. (1982) Int. Biodeterioration Bull. 18[1]:7-12).

Accordingly, what is needed in the art is biocidal composition that offers the biocidal efficacy of pyrithione and its derivatives against free-living microorganisms and biofilms, that is highly efficacious and cost-effective, but without environmental and toxicological effects. The present invention is believed to be an answer to that need.

SUMMARY OF THE INVENTION

In one aspect, the present invention is directed to an antimicrobial composition, comprising: pyrithione or a pyrithione complex; and a zinc or copper or silver source selected from the group consisting of zinc or copper or silver salts, zinc or copper or silver oxides, zinc or copper or silver hydroxides, zinc or copper or silver sulfates, zinc or copper or silver chlorides, zinc or copper or silver metals, zinc or copper or silver complexes, and combinations thereof; wherein the weight ratio of the zinc or copper or silver source to the pyrithione or the pyrithione complex is in the range from about 1:300 to about 50:1, and wherein the antimicrobial composition has an enhanced biocidal effect against microorganisms selected from the group consisting of free-living microorganisms, parasitic microorganisms, adherent microorganisms, biofilms, and combinations thereof.

In another aspect, the present invention is directed to a method of inhibiting the growth of microorganisms selected from the group consisting of free-living microorganisms, parasitic microorganisms, adherent microorganisms, biofilms, and combinations thereof, comprising the step of contacting the microorganisms with an antimicrobial composition comprising pyrithione or a pyrithione complex; and a zinc or copper or silver source selected from the group consisting of zinc or copper or silver salts, zinc or copper or silver oxides, zinc or copper or silver hydroxides, zinc or copper or silver sulfates, zinc or copper or silver chlorides, zinc or copper or silver metals, zinc or copper or silver complexes, and combinations thereof; wherein the weight ratio of the zinc or copper or silver source to the pyrithione or the pyrithione complex is in the range from about 1:300 to about 50:1, and wherein the antimicrobial composition has an enhanced biocidal effect against the microorganisms.

In yet another aspect, the present invention is directed to a fuel, fluid, or lubricant, comprising water or an organic base fluid and an antimicrobial composition, the antimicrobial composition comprising pyrithione or a pyrithione complex; and a zinc or copper or silver source selected from the group consisting of zinc or copper or silver salts, zinc or copper or silver oxides, zinc or copper or silver hydroxides, zinc or copper or silver sulfates, zinc or copper or silver chlorides, zinc or copper or silver metals, zinc or copper or silver complex, and combinations thereof; wherein the weight ratio of the zinc or copper or silver source to the pyrithione or the pyrithione complex is in the range from about 1:300 to about 50:1, and wherein the antimicrobial composition has an enhanced biocidal effect against microorganisms selected from the group consisting of free-living microorganisms, parasitic microorganisms, adherent microorganisms, biofilms, and combinations thereof.

In yet another aspect, the present invention is directed to a coated substrate comprising a substrate together with a coating on the substrate, the coating being produced by: (a) contacting the substrate with a coating composition comprising pyrithione or a pyrithione complex; and a zinc or copper or silver source selected from the group consisting of zinc or copper or silver salts, zinc or copper or silver oxides, zinc or copper or silver hydroxides, zinc or copper or silver sulfates, zinc or copper or silver chlorides, zinc or copper or silver metals, zinc or copper or silver complexes, and combinations thereof; wherein the weight ratio of the zinc or copper or silver source to the pyrithione or the pyrithione complex is in the range from about 1:300 to about 50:1, and wherein the antimicrobial composition has an enhanced biocidal effect against microorganisms selected from the group consisting of free-living microorganisms, parasitic microorganisms, adherent microorganisms, biofilms, and combinations thereof; and (b) drying the coating composition on the substrate to produce the coated substrate.

In yet another aspect, the present invention is directed to a coating composition, comprising: (a) a base medium comprising water or a solvent resin system selected from the group consisting of vinyl, alkyd, epoxy, acrylic, polyurethane and polyester resins, and combinations thereof; and (b) a biocide comprising an antimicrobial composition consisting essentially of pyrithione or a pyrithione complex; and a zinc or copper or silver source selected from the group consisting of zinc or copper or silver salts, zinc or copper or silver oxides, zinc or copper or silver hydroxides, zinc or copper or silver sulfates, zinc or copper or silver chlorides, zinc or copper or silver metals, zinc or copper or silver complexes, and combinations thereof; wherein the weight ratio of the zinc or copper or silver source to the pyrithione or the pyrithione complex is in the range from about 1:300 to about 50:1, and wherein the antimicrobial composition has an enhanced biocidal effect against microorganisms selected from the group consisting of free-living microorganisms, parasitic microorganisms, adherent microorganisms, biofilms, and combinations thereof.

In yet another aspect, the present invention is directed to a composition comprising a plastic or a woven or non-woven fiber, or a textile which comprises, in combination, a plastic or a fiber and an antimicrobial composition consisting essentially of pyrithione or a pyrithione complex; and a zinc or copper or silver source selected from the group consisting of zinc or copper or silver salts, zinc or copper or silver oxides, zinc or copper or silver hydroxides, zinc or copper or silver sulfates, zinc or copper or silver chlorides, zinc or copper or silver metals, zinc or copper or silver complexes, and combinations thereof; wherein the weight ratio of the zinc or copper or silver source to the pyrithione or the pyrithione complex is in the range from about 1:300 to about 50:1, and wherein the antimicrobial composition has an enhanced biocidal effect against microorganisms selected from the group consisting of free-living microorganisms, parasitic microorganisms, adherent microorganisms, biofilms, and combinations thereof.

In yet another aspect, the present invention is directed to an antimicrobial composition for treating microorganisms selected from the group consisting of free-living microorganisms, parasitic microorganisms, adherent microorganisms, biofilms, and combinations thereof, comprising: a salt of pyrithione; and a zinc metal salt; wherein the weight ratio of the water-soluble zinc metal salt to the salt of pyrithione is in the range from about 1:300 to about 50:1, and wherein the antimicrobial composition has an enhanced biocidal effect against free-living microorganisms, parasitic microorganisms, adherent microorganisms, biofilms, and combinations thereof.

In yet another aspect, the present invention is directed to an adhesive composition, comprising: (a) an adhesive base medium; and (b) a biocide comprising an antimicrobial composition consisting essentially of pyrithione or a pyrithione complex; and a zinc or copper or silver source selected from the group consisting of zinc or copper or silver salts, zinc or copper or silver oxides, zinc or copper or silver hydroxides, zinc or copper or silver sulfates, zinc or copper or silver chlorides, zinc or copper or silver metals, zinc or copper or silver complexes, and combinations thereof; wherein the weight ratio of the zinc or copper or silver source to the pyrithione or the pyrithione complex is in the range from about 1:300 to about 50:1, and wherein the antimicrobial composition has an enhanced biocidal effect against microorganisms selected from the group consisting of free-living microorganisms, parasitic microorganisms, adherent microorganisms, biofilms, and combinations thereof.

In yet another aspect, the present invention is directed to an elastomer composition, comprising: (a) an elastomeric base medium; and (b) a biocide comprising an antimicrobial composition consisting essentially of pyrithione or a pyrithione complex; and a zinc or copper or silver source selected from the group consisting of zinc or copper or silver salts, zinc or copper or silver oxides, zinc or copper or silver hydroxides, zinc or copper or silver sulfates, zinc or copper or silver chlorides, zinc or copper or silver metals, zinc or copper or silver complexes, and combinations thereof; wherein the weight ratio of the zinc or copper or silver source to the pyrithione or the pyrithione complex is in the range from about 1:300 to about 50:1, and wherein the antimicrobial composition has an enhanced biocidal effect against microorganisms selected from the group consisting of free-living microorganisms, parasitic microorganisms, adherent microorganisms, biofilms, and combinations thereof.

In yet another aspect, the present invention is directed to a sealant composition, comprising: (a) a sealant base medium; and (b) a biocide comprising an antimicrobial composition consisting essentially of pyrithione or a pyrithione complex; and a zinc or copper or silver source selected from the group consisting of zinc or copper or silver salts, zinc or copper or silver oxides, zinc or copper or silver hydroxides, zinc or copper or silver sulfates, zinc or copper or silver chlorides, zinc or copper or silver metals, zinc or copper or silver complexes, and combinations thereof; wherein the weight ratio of the zinc or copper or silver source to the pyrithione or the pyrithione complex is in the range from about 1:300 to about 50:1, and wherein the antimicrobial composition has an enhanced biocidal effect against microorganisms selected from the group consisting of free-living microorganisms, parasitic microorganisms, adherent microorganisms, biofilms, and combinations thereof.

In yet another aspect, the present invention is directed to a skin care composition, comprising: (a) a skin care base; and (b) a biocide comprising an antimicrobial composition consisting essentially of pyrithione or a pyrithione complex; and a zinc or copper or silver source selected from the group consisting of zinc or copper or silver salts, zinc or copper or silver oxides, zinc or copper or silver hydroxides, zinc or copper or silver sulfates, zinc or copper or silver chlorides, zinc or copper or silver metals, zinc or copper or silver complexes, and combinations thereof; wherein the weight ratio of the zinc or copper or silver source to the pyrithione or the pyrithione complex is in the range from about 1:300 to about 50:1, and wherein the antimicrobial composition has an enhanced biocidal effect against microorganisms selected from the group consisting of free-living microorganisms, parasitic microorganisms, adherent microorganisms, biofilms, and combinations thereof.

In yet another aspect, the present invention is directed to a method of preserving cellulose-based material, comprising the steps of: contacting a cellulose-based material with an antimicrobial composition, comprising pyrithione or a pyrithione complex; and a zinc or copper or silver source selected from the group consisting of zinc or copper or silver salts, zinc or copper or silver oxides, zinc or copper or silver hydroxides, zinc or copper or silver sulfates, zinc or copper or silver chlorides, zinc or copper or silver metals, zinc or copper or silver complexes, and combinations thereof; wherein the weight ratio of the zinc or copper or silver source to the pyrithione or the pyrithione complex is in the range from about 1:300 to about 50:1, and wherein the antimicrobial composition has an enhanced biocidal effect against microorganisms selected from the group consisting of free-living microorganisms, parasitic microorganisms, adherent microorganisms, biofilms, and combinations thereof.

In yet another aspect, the present invention is directed to a method of preserving detergents or surfactants, comprising the steps of: contacting a detergent or surfactant with an antimicrobial composition, comprising: pyrithione or a pyrithione complex; and a zinc or copper or silver source selected from the group consisting of zinc or copper or silver salts, zinc or copper or silver oxides, zinc or copper or silver hydroxides, zinc or copper or silver sulfates, zinc or copper or silver chlorides, zinc or copper or silver metals, zinc or copper or silver complexes, and combinations thereof; wherein the weight ratio of the zinc or copper or silver source to the pyrithione or the pyrithione complex is in the range from about 1:300 to about 50:1, and wherein the antimicrobial composition has an enhanced biocidal effect against microorganisms selected from the group consisting of free-living microorganisms, parasitic microorganisms, adherent microorganisms, biofilms, and combinations thereof.

In yet another aspect, the present invention is directed to a pharmaceutical composition, comprising: (a) a pharmaceutically acceptable carrier; and (b) an antimicrobial composition, comprising pyrithione or a pyrithione complex; and a zinc or copper or silver source selected from the group consisting of zinc or copper or silver salts, zinc or copper or silver oxides, zinc or copper or silver hydroxides, zinc or copper or silver sulfates, zinc or copper or silver chlorides, zinc or copper or silver metals, zinc or copper or silver complexes, and combinations thereof; wherein the weight ratio of the zinc or copper or silver source to the pyrithione or the pyrithione complex is in the range from about 1:300 to about 50:1, and wherein the antimicrobial composition has an enhanced biocidal effect against microorganisms selected from the group consisting of free-living microorganisms, parasitic microorganisms, adherent microorganisms, biofilms, and combinations thereof.

These and other aspects will become apparent upon reading the following detailed description of the invention.

BRIEF DESCRIPTION OF THE FIGURES

The invention will be more fully understood from the following detailed description taken in conjunction with the accompanying drawings, in which.

DETAILED DESCRIPTION OF THE INVENTION

Figure 1:
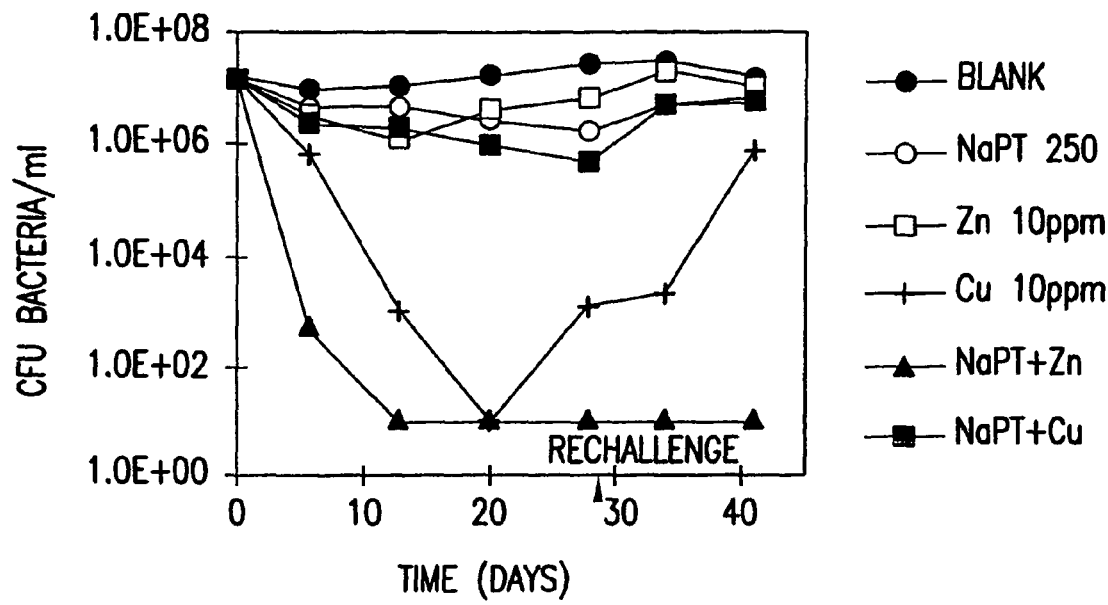
FIG. 1 is a graph showing the antibacterial efficacy of sodium pyrithione plus Cu(II) or Zn(II) in a metalworking fluid.

It now has been surprisingly found, in accordance with the present invention, that a solution is provided to the problem of providing a biocidal composition that possesses enhanced biocidal efficacy relative to of pyrithione or its derivatives alone. The present inventors have solved this problem by developing an antimicrobial composition comprising pyrithione or a pyrithione complex in combination with a zinc or copper or silver source, for example, a copper salt and/or a zinc salt and/or a silver salt. The composition of the invention displays an enhanced biocidal effect, relative to pyrithione alone, on a wide range microorganisms in both the free-living and biofilm state. This antimicrobial performance is greater than might be expected based upon the additive effect of the individual components of this composition. The enhanced biocidal effectiveness associated with the composition of the present invention permits the use of smaller amounts of the pyrithione component of the present composition, as compared to the conventionally employed amounts of pyrithione-based biocides. The reduction in pyrithione amount, in turn, results in more effective elimination of a wide range of free-living microorganisms, parasitic microorganisms, adherent microorganisms, biofilms, and combinations thereof at a lower cost.

As defined herein, the term "enhanced biocidal effect" refers to an interaction between the pyrithione or pyrithione salt component and the metal ion source of the composition that results in the biocidal effect of the composition being greater than either of the components taken individually. Thus, the antimicrobial results exceed the expected biocidal effect of the combination based upon the performance of the individual components.

As defined herein, the term "skin care composition" refers to materials applied topically to the skin that benefit, improve, or enhance the condition of the skin, or treat skin suffering from an infectious or diseased condition. Such skin care compositions include bases such as soap bases, cosmetic bases, medicament bases, cream bases, emollient bases, and combinations thereof, as well as other bases known in the art.

The following discussion elaborates on several particular features of biofilms. As defined herein, the term "biofilm" refers to any aggregate of cells anchored to one another, or to surfaces, by extracellular slime. While most unicellular organisms produce a protective coating of slime, cells aggregated into biofilms are physically different from free-living cells and produce much more extracellular slime than free-living cells. The slime structures which make up part of the biofilm are quite complex both biologically and architecturally. They are composed of discreet microbial aggregates (microcolonies) separated by water channels which can form large tower-shaped or mushroom-shaped structures. As biofilms develop, free-living cell detach from the biofilm and migrate through the environment in search of new areas the colonize and form new biofilm. In metalworking fluids, a buildup of biofilms can cause many problems, including fluid deterioration/degradation, foul odors, corrosion, clogging of filters, transfer lines, nozzles, and crevices, fouling of machine surfaces, machine down-time, shorter tool life, fouling and damage of the workpiece, and the like. As mentioned above, biofilms can also enhance the rate of degradation of other fluids such as paints or other surface coatings. Medical equipment, such as cardiac implants, catheters, dialysis machines, dental waterlines, and the like, may also become contaminated by biofilms and spread infection.

Biofilms possess extensive physical and chemical heterogeneity which is not found in the free-living cells residing in bulk fluid. Because biofilm cells are in intimate contact with one another in the biofilm, ecological interaction between the individual organisms can become complex and extensive. Due to the high degree of complexity and heterogeneity that is present in a biofilm, biofilm cells possess dramatically different metabolic parameters as compared to free-living cells (e.g., metabolic rate, growth rate, preference for specific nutrients, etc.). In addition, cells found in biofilms generally display a greater diversity of species and organism types as compared to free-living cells found in bulk fluid.

As indicated above, the present invention is directed to an antimicrobial composition, comprising pyrithione or a pyrithione complex; and a zinc or copper or silver source selected from the group consisting of zinc or copper or silver salts, zinc or copper or silver oxides, zinc or copper or silver hydroxides, zinc or copper or silver sulfates, zinc or copper or silver chlorides, zinc or copper or silver metals, zinc or copper or silver complexes, and combinations thereof; wherein the weight ratio of the zinc or copper or silver source to the pyrithione or the pyrithione complex is in the range from about 1:300 to about 50:1, and wherein the antimicrobial composition has an enhanced biocidal effect against microorganisms selected from the group consisting of free-living microorganisms, parasitic microorganisms, adherent microorganisms, biofilms, and combinations thereof. Each of these components will be discussed in more detail below.

Pyrithione in its acid form, or a pyrithione complex may be used in the composition of the present invention. As defined herein, the term "pyrithione complex" refers to combinations of one or more pyrithione molecules and one or more metal or ligands, such as pyrithione salts and adducts of pyrithione.

Examples of pyrithione salts that are useful in the present composition include sodium pyrithione, potassium pyrithione, lithium pyrithione, ammonium pyrithione, zinc pyrithione, copper pyrithione, calcium pyrithione, magnesium pyrithione, strontium pyrithione, silver pyrithione, gold pyrithione, manganese pyrithione, and combinations thereof. Non-metal pyrithione salts such as the ethanolamine salt, chitosan salt, and the disulfide salt of pyrithione (which is commercially available as OMADINE MDS or OMDS), may also be used. The two most preferred salts of pyrithione useful in the present invention are the sodium salt (i.e., sodium pyrithione) and zinc pyrithione. Sodium pyrithione is a well-known commercial product that is commonly made by reacting 2-chloropyridine-N-oxide with NaSH and NaOH, as illustrated in the disclosure of U.S. Pat. No. 3,159,640. Zinc pyrithione may be made by reacting 1-hydroxy-2-pyridinethione (i.e., pyrithione acid) or a soluble salt thereof with a zinc salt (e.g., zinc sulfate) to form a zinc pyrithione precipitate, as illustrated in U.S. Pat. No. 2,809,971.

Examples of useful pyrithione adducts include 2,2'-dithiopyridine-1,1'-dioxide (also known as omadine disulfide) and alkali or alkaline earth complexes of 2,2'-dithiopyridine-1,1'-dioxide (e.g., the magnesium salt of 2,2'-dithiopyridine-1,1'-dioxide, also known as magnesium pyrithione disulfide or MDS).

Zinc or copper or silver sources useful in the composition of the present invention include, for example, raw zinc or copper or silver metal, zinc or copper or silver salts, zinc or copper or silver oxides, zinc or copper or silver hydroxides, zinc or copper or silver sulfates, zinc or copper or silver chlorides, zinc or copper or silver complexes, and combinations thereof. As defined herein, the term "complexes" refers to an association of a metal ion with a complexing agent (typically an organic or inorganic ligand). Examples of complexing agents include, but are not limited to, zeolites, titania, carbon, or other inert support, azoles, EDTA (ethylenediaminetetraacetic acid), EGTA (ethylene-bis-(oxyethylenenitrilo)-tetra-acetic acid), crown ethers, cryptates, cyclodextrins, and the like. Zinc or copper or silver sources used in the composition of the present invention may also be electrolytically generated, for example from a silver or copper or zinc anode.

Examples of zinc salts that may be used in the composition of the present invention include zinc acetate, zinc oxide, zinc carbonate, zinc hydroxide, zinc chloride, zinc sulfate, zinc citrate, zinc fluoride, zinc iodide, zinc lactate, zinc oleate, zinc oxalate, zinc phosphate, zinc propionate, zinc salicylate, zinc selenate, zinc silicate, zinc stearate, zinc sulfide, zinc tannate, zinc tartrate, zinc valerate, zinc gluconate, zinc undecylate, and the like. Combinations of zinc salts may also be used in the composition of the invention.

Examples of suitable copper salts include copper disodium citrate, copper triethanolamine, copper carbonate, cuprous ammonium carbonate, cupric hydroxide, copper chloride, cupric chloride, copper ethylenediamine complex, copper oxychloride, copper oxychloride sulfate, cuprous oxide, copper thiocyanate, and the like. Combinations of these copper salts may also be used in the composition of the invention. In addition, combinations of copper salts and zinc salts may also be used in the composition of the invention.

A variety of forms of silver may also be used in the composition of the invention. Examples of useful silver species include colloidal silver, silver salts, and silver complexes, such as silver bromide, silver chloride, silver citrate, silver iodide, silver lactate, silver nitrate, silver oxide, silver picrate, and the like.

In addition, other metal ions may be useful in the composition of the present invention as a metal ion source. Other useful metal ions include titanium, cobalt, cadmium, chromium, manganese, platinum, palladium, vanadium, and the like.

Useful amounts of the zinc or copper or silver salts to pyrithione or pyrithione salts range from about 1:300 to about 50:1, and more preferably from about 1:100 to about 1:10, and more preferably from about 1:100 to about 1:1, each ratio expressed on a weight:weight basis.

The composition of the invention can be made by mixing one or more selected zinc or copper or silver sources and one or more pyrithione or pyrithione complexes in an appropriate media or carrier, or by adding the individual components separately to the functional blend or fluid being treated to impart antimicrobial protection. Useful media or carriers for the composition include aqueous media such as water, or water in combination with one or more organic solvent(s). Useful organic solvents include alcohols, such as methanol, ethanol, alkanolamines, ethers such as glycol ethers, esters, and the like.

The antimicrobial composition of the invention is useful as an algaecide, bactericide, fungicide, insecticide, protozoacide, and/or nematocide, and is particularly useful in inhibiting the growth of free-living microorganisms (including saprophytic microorganisms) parasitic microorganisms (including intracellular, multicellular, and unicellular microorganisms), adherent microorganisms, biofilms, and combinations thereof. Examples of microorganisms that are effectively treated by the composition of the invention include *Pseudomonas aeruginosa, Aspergillus niger, Fusarim, Cephalosporium, Pseudomonas fluorescens, Pseudomonas rubescens, Pseudomonas stutzeri, Pseudomonas olevorans, Alcaligenes faecalis, Escherichia coli, Citrobacter freundii, Staphylococcus aureus, Candida albicans, Pityrosporum ovale* and the like. The antimicrobial composition of the invention is a useful additive in industrial fluids (e.g., metalworking fluids), paints, coatings, adhesives, sealants, elastomers, personal care products (e.g., antidandruff shampoos, soaps, skin-care medicaments, cosmetics, and the like), swimming pool products, wood products, plastic products, medical products, woven or nonwoven fibers (e.g., cotton, wool, silk, linen, leather, and the like), textiles, or any other application where microorganism growth, and particularly biofilm growth, must be stopped or slowed.

One significant use application for the antimicrobial compositions of the present invention is in fuels, fluids, or lubricants, such as metalworking fluids, cutting fluids, engine fluids, transmission fluids, and the like. These functional fluids are typically supplied as a concentrate containing the antimicrobial composition and the other components of the functional fluid. In the concentrate, a sufficient amount of the antimicrobial composition is provided such that the "working" functional fluid will contain a biocidally effective amount thereof. In order to satisfy this requirement, the concentrate for a metalworking fluid, for example, preferably contains a total amount of up to about 15 weight percent, or more, of the antimicrobial composition, thereby providing up to about 1,500 ppm, or more, of the antimicrobial composition in the working fluid based upon a dilution rate of the concentrate to the working fluid of between about 1:10 and about 1:100.

The antimicrobial compositions of the present invention are also useful in coatings such as paints, including indoor and outdoor household paints, industrial and commercial paints. Particularly advantageous results are obtained when the antimicrobial compositions of the present invention are utilized, preferably in a total amount of between about 0.01% and about 10% by weight based upon the weight of the paint, as in-can preservatives during storage and prior to the use of the paint. Although the antimicrobial compositions are also suitable for use in conjunction with marine paints for use, for example, on ship's hulls, care should be taken to avoid leaching of the soluble components of the composition out of the paint. Leaching can be suitably controlled by the use of known encapsulation techniques.

The paint composition of the present invention may be used as a paint for natural or synthetic materials, for example wood, paper, metals, textiles and plastics. It is particularly suitable as an outdoor paint, and is excellent for use as a marine paint.

In addition to paints, the antimicrobial composition of the present invention is also useful as an additive to other coatings known in the art. For example, the antimicrobial composition of the invention may be added to a coating made from a base of a urethane polymer dispersion mixture, a hydroxylated methylmethacrylate acrylic polymer emulsion, and a crosslinker to form a coating that is resistant to microbial growth.

The antimicrobial composition of the present invention is also useful as an additive in adhesives, particularly water-based adhesives, to slow or stop microbial growth. The water-based nature of this type of adhesive alleviates the use and disposal of toxic organic compounds. Government regulation of the use and disposal of toxic organic substances has forced many manufacturers to turn to water-based compositions. In addition, the water-based nature of this type of adhesive composition results in less volatile organic fumes being given off during application and drying processes.

In one embodiment, the antimicrobial composition of the present invention may be added to a water-based adhesive base made from, among other things, a combination of water-based aliphatic urethane resins. In another embodiment, the antimicrobial composition of the present invention may be added to a water-based adhesive base made from, among other things, a styrene-butadiene/latex (termed "SBR") dispersion and an aqueous aliphatic polyurethane dispersion. As an example, the following adhesive base medium may be used:

| COMPONENT | WET PARTS |
| --- | --- |
| Oil | 55.0 |
| Hydrocarbon resin | 45.0 |
| Rosin Acid | 10.0 |
| Surfactant | 1.6 |
| Urea | 2% dry/dry |
| Potassium Hydroxide | 40.0 |
| clay slurry | 190 |
| SBR latex | 94 |
| Polyacrylate thickener | 18.0 |

It will be appreciated, however, that any adhesive base may be used in combination with the antimicrobial composition of the present invention.

The antimicrobial composition of the present invention may also be added to a sealant or an elastomer to provide control or eliminate microbial growth in those compositions. Known sealant or elastomer compositions typically include a base medium made from urethane, polyurethane, or a urethane prepolymer, and are frequently combined with catalysts or other agents to give the sealant or elastomer composition desired qualities. Other sealants and elastomers are known to be made from conjugated dienes, styrene-butadiene copolymers, styrene polymers, random copolymers of conjugated dienes and vinyl aromatic hydrocarbons, chloroprenes (e.g., neoprenes), isoprenes (e.g., natural latex), polyacrylates, and polysiloxanes (e.g., silicone rubbers). Examples of sealant and elastomer base compositions are provided in U.S. Pat. Nos. 4,374,237; 4,687,533; 4,374,237; 5,844,021; 4,410,644; 4,595,724; and 4,925,894.

The compositions of the present invention are useful, in any of the variety of applications described herein, as disinfectants and preservatives, in a liquid or spreadable solid form, alone or in combination with an inert carrier such as water, liquid hydrocarbons, ethanol, isopropanol, or the like. The antimicrobial composition of the present invention is particularly useful in a soap, skin care, or cosmetic base to act as a preservative. The composition of the invention can be employed using conventional procedures to control bacteria and fungi in various substrates, and can be applied to bacterial or fungal organisms or their substrates in an antimicrobial amount by conventional procedures such as spraying, dipping, drenching impregnation, and the like.

The composition of the present invention is also useful as a preservative for wood or other cellulose-based materials, such as lumber, paper, cardboard, and the like, where microbial growth can occur. Examples of uses of the present invention in the preservation of wood and cellulose-based materials include, but are not limited to, lumber found on docks, ship hulls, patio decks, storage pallets, or other building and/or structural materials. The composition of the present invention may also be used as a preservative for detergents and/or surfactants, such as ionic, nonionic, and zwitterionic detergents or surfactants commonly known in the art and in which microorganism growth is problematic The composition of the present invention may also be used as a pharmaceutical composition to control the growth of any of the above microbial organisms in a patient suffering from their systemic infection. The pharmaceutical composition of the invention is preferably administered internally, e.g., intravenously, in the form of conventional pharmaceutical preparations, for example in conventional enteral or parenteral pharmaceutically acceptable carriers, such as water, gelatin, lactose, starch, magnesium stearate, talc, plant oils, gums, alcohol, Vaseline, or the like. The pharmaceutical composition can be in conventional solid forms, for example, tablets, dragees, suppositories, capsules, or the like, or conventional liquid forms, such as suspensions, emulsions, or the like. If desired, they can be sterilized and/or contain conventional pharmaceutical adjuvants, such as preservatives, stabilizing agents, wetting agents, emulsifying agents, buffers, or salts used for the adjustment of osmotic pressure. The pharmaceutical preparations may also contain other therapeutically active materials. The pharmaceutical preparation of the invention should include an amount of the compound of the invention effective for antimicrobial activity. The effective dosage will depend on the antimicrobial activity and toxicity of the particular compound employed and is thus within the ordinary skill of the art to determine for any particular host mammal or other host organism. Suitable dosages may be, for example, in the range of about 0.5-15 mg per kg for a human being.

The present invention permits the use of reduced amounts of the pyrithione primary biocide, in conjunction with a water-soluble metal salt co-biocide that is less expensive than the primary biocide, thereby providing an antimicrobial composition that is inexpensive to produce and that possesses the above-mentioned characteristic of enhanced antimicrobial effectiveness against a variety of microorganisms.

The following examples are intended to illustrate, but in no way limit the scope of the present invention. All parts and percentages are by weight and all temperatures are in degrees Celsius unless explicitly stated otherwise.

EXAMPLES

Example 1

The Effect of 0.5 ppm Cu (II) on the Minimum Inhibitory Concentration (MIC) of Sodium Pyrithione (NaPT)

NaPT and copper pyrithione ($CuPT_2$) were serially diluted in microtiter plates in Tryptic Soy Broth (TSB). NaPT was also diluted in TSB amended with 1 ppm of Cu (II) ($CuSO_4 \cdot 5H_2O$). Equal volumes of bacterial suspension ($10^6$ bacteria per milliliter of TSB) containing *Pseudomonas aeruginosa* ATCC 9027 or fungal spore suspension ($10^5$ spores per milliliter of TSB) containing *Aspergillus niger* ATCC 6275 or species of *Fusarium* and *Cephalosporium* isolated from contaminated metalworking fluid were added to each microtiter plate well, and the plates were incubated at 28° C. Controls were prepared for cultures inoculated into TSB with and without Cu (II). After a period of 4 to 8 days, the lowest concentration of biocide causing the inhibition of visible growth was observed. The results are shown in Table 1.

As shown in Table 1, Cu (II) had no effect by itself or on the MIC of NaPT against the bacterium, but it reduced the MIC-NaPT four to sixteen-fold for the fungi. The pH of the broth medium was not influenced by the copper ion.

The antifungal effect of $CuPT_2$ for *Aspergillus niger* was greater than that of NaPT. The molar MIC of $CuPT_2$ (0.051 mM) was one seventeenth of that of NaPT. However, the amount of $CuPT_2$ (0.008 mM) theoretically formed in the mixture (0.5 ppm Cu (II) +8 ppm NaPT) was significantly less than the MICCUPT2. Thus, the enhancement of NaPT biocidal activity cannot be attributed simply to the formation of the more active $CuPT_2$ species.

TABLE 1

| | | MIC (ppm) | | |
|---|---|---|---|---|
| Test Organism* | Cu (II) | NaPT (without Cu) | NaPT (with 0.5 ppm Cu) | $CuPT_2$ |
| Bacteria: | | | | |
| *Pseudomonas aeruginosa* | >0.5 | 256 | 256 | >1024 |
| Fungi: | | | | |
| *Aspergillus niger* | >0.5 | 128 | 8 | 16 |
| *Fusarium* sp. | >0.5 | 256 | 8 | — |
| *Cephalosporium* sp. | >0.5 | 64 | 16 | — |

*P. aeruginosa* was incubated 5-6 days; *A. niger* was incubated 7-8 days; *Fusarium* and *Cephalosporium* were incubated 5 days.

Example 2

Interactions of Pyrithione Salts and Zn(II) Ion: Zone of Inhibition Test

Cultures of bacteria were grown for 24 hr. on Tryptic Soy Agar (TSA), and suspensions containing $10^8$ cells per milliliter of sterile water were prepared. TSA plates were inoculated with sterile cotton swabs, and sterile 6.5 mm paper discs soaked with solutions containing solutions of 0.135% pyrithione (NaPT and the $MgSO_4 \cdot 3H_2O$ adduct of 2,2'-dithiopyridine-1,1'-dioxide (MDS) in water, or zinc pyrithione (ZPT) in dimethylsulfoxide (DMSO)), 0.10% $ZnCl_2$, or a 1:1 molar mixture of pyrithione and $ZnCl_2$. The discs were applied, and the plates were incubated at 28° C. for 24 hr. The diameter of each zone of inhibition was measured with a ruler. The results are shown in Table 2.

As shown in Table 2, zinc chloride, by itself produced no zone of inhibition for any of the three cultures and decreased the zone of inhibition for some mixtures, but it increased the zone of inhibition of MDS for *Pseudomonas aeruginosa*, indicating a favorable effect.

TABLE 2

| | Zone of Inhibition (mm) | | |
|---|---|---|---|
| Test Solution | *Staphylococcus aureus* ATCC 27217 | *Escherichia coli* ATCC 10536 | *Pseudomonas aeruginosa* NCIMB 6749 |
| DMSO | 0 | 0 | 0 |
| $ZnCl_2$, 0.1% | 0 | 0 | 0 |
| NaPT, 0.135% | 31 | 35 | 8 |
| ZPT, 0.135% | 27 | 31 | 10 |
| MDS, 0.135% | 28 | 31 | 0 |
| NaPT, 0.135% + $ZnCl_2$, 0.1% | 27 | 24 | 8 |
| ZPT, 0.135% + $ZnCl_2$, 0.1% | 26 | 27 | 10 |
| MDS, 0.135% + $ZnCl_2$, 0.1% | 28 | 32 | 9 |

Example 3

Interactions of Pyrithione Salts and Zn(II) and Ag(I) Ion: Checkerboard Minimum Inhibitory Concentration Test

Mixtures of pyrithione and zinc or silver in various proportions were tested for relative efficacy by a modification of the procedure described by Dougherty, et al.

To evaluate Zn ion (Table 3a), aqueous stock solutions of pyrithione and zinc salts ($ZnSO_4$ or ZnO) and mixtures of the two were serially diluted in TSB in microtiter plates. Equal volumes of bacteria ($10^6$ cells/ml) or fungi ($10^5$ spores/ml) were added to each microtiter plate well. The plates were incubated at 28 C for 3 days (bacteria) or 5 days (fungi), and the minimum inhibitory concentration (MIC) of biocide was determined. The Fractional Inhibitory Concentration (FIC=concentration of biocide in an inhibitory mixture divided by the MIC of the pure biocide) was determined, and the FIC Index (sum of the two FIC's) was calculated. The type of interaction was categorized according to the magnitude of the Index: Synergistic (<1), Additive (1), or Antagonistic (>1).

TABLE 3a

Interaction of Pyrithiones with Zinc Salts
MIC (ppm)

| Test Organism | Pyrithione salt | Zn(II) | Pyrithione | Zn(II)/ pyrithione | FIC Index |
|---|---|---|---|---|---|
| *Staphylococcus aureus* ATCC 27217 | NaPT + ZnSO₄ | 200 | 0 | — | — |
| | | 50 | ≤1 | ≧50/1 | ≤0.5 |
| | | 25 | ≤1 | ≧25 | ≤0.8 |
| | | 12.5 | 2 | 6/1 | 0.6 |
| | | 6.3-0.8 | 4 | 2/1-1/5 | 1.0 |
| | | 0 | 4 | — | — |
| | ZPT + ZnSO₄ | 200 | 0 | — | — |
| | | 50 | 1 | 50/1 | 0.5 |
| | | 25-12.5 | 2 | 13/1-6/1 | 0.6-0.6 |
| | | 6.3-0.8 | 4 | 2/1-1/5 | 1.0 |
| | | 0 | 4 | — | — |
| | MDS + ZnSO₄ | 200 | 0 | — | — |
| | | 50 | 1 | 50/1 | 0.4 |
| | | 25 | 2 | 13/1 | 0.3 |
| | | 12.5-6.3 | 4 | 3/1-2/1 | 0.5-0.6 |
| | | 3.1-0.8 | 8 | 1/3-1/10 | 1.0 |
| | | 0 | 8 | — | — |
| *Pseudomonas aeruginosa* NCIMB 6749 | NaPT + ZnSO₄ | >200 | 0 | — | — |
| | | 50 | 8 | 6/1 | <0.3 |
| | | 25 | 16 | 2/1 | <0.3 |
| | | 12.5 | 64 | 1/5 | <0.6 |
| | | 6.3-0.8 | 128 | 1/20-1/160 | <1.0 |
| | | 0 | 128 | — | — |
| | ZPT + ZnSO₄ | >200 | 0 | — | — |
| | | 50-12.5 | 16 | 3/1-1/1 | <(0.1-0.3) |
| | | 6.3 | 128 | 1/20 | <0.5 |
| | | 3.1-0.8 | 256 | 83/1-320/1 | <1.0 |
| | | 0 | 256 | — | — |
| | MDS + ZnSO₄ | <200 | 0 | — | — |
| | | 50-25 | 32 | 2/1-1/1 | <(0.2-0.3) |
| | | 12.5 | 128 | 1/10 | <0.2 |
| | | 6.3 | 512 | 1/81 | <0.5 |
| | | 3.1-0.8 | 1024 | 1/330-1/1280 | <1.0 |
| | | 0 | 1024 | — | — |
| *Fusarium* sp. | NaPT + ZnSO₄ | >200 | 0 | — | — |
| | | 50-6.3 | 51 | 1/1-1/8 | <(0.2-0.4) |
| | | 3.1-1.6 | 103 | 1/33-1/64 | <0.3 |
| | | 0.8 | 205 | 1/256 | <0.5 |
| | | 0 | 411 | — | — |
| | ZPT + ZnSO₄ | <200 | 0 | — | — |
| | | 50-25 | 256 | 1/5-1/10 | <(4.1-4.3) |
| | | 12.5 | 128 | 1/10 | <2.1 |
| | | 6.3 | 64 | 1/10 | <1.0 |
| | | 3.1 | 128 | 1/41 | <2.0 |
| | | 1.6-0.8 | 64 | 1/40-1/80 | <1.0 |
| | | 0 | 64 | — | — |
| | MDS + ZnSO₄ | >200 | 0 | — | — |
| | | 50-6.3 | 115 | 1/2-1/18 | <(0.1-0.3) |
| | | 3.1 | 230 | 1/75 | <0.2 |
| | | 1.6 | 461 | 1/288 | <0.3 |
| | | 0.8 | 1843 | 1/2300 | <1.0 |
| | | 0 | >1843 | — | — |
| *Ps. aeruginosa* ATCC 9027 | ZPT + ZnO | >1645 | 0 | — | — |
| | | 51 | 64 | 1/1 | <0.16 |
| | | 0 | 512 | — | — |
| *Aspergillus niger* ATCC 6275 | ZPT + ZnO | >1645 | 0 | — | — |
| | | 206 | 32 | 6/1 | <0.63 |
| | | 0 | 64 | — | — |

Consistent with the previous example, Zn(II) enhanced the activity of MDS. The FIC Indices were <1 for the Zn(II)/MDS range of from 1/288 to 50/1 for two bacteria and one fungus (Table 3a). However, the interaction was not technically synergistic, because the Zn²⁺ reagent by itself produced no detectable effect at the concentrations used. In contrast to results in Example 1, Zn(II) surprisingly enhanced by activities of the two other pyrithiones. The FIC Indices were <1.0 for the Zn(II)/pyrithione range of from 1/256 to ≧50/1.

The zinc complex of pyrithione (ZPT) and the sodium salt of pyrithione (NaPT) and silver salts were tested in various ratios according to the checkerboard procedure described above. Briefly, mixtures of pyrithiones and silver ions in various proportions were tested for relative efficacy by the modified procedure of Dougherty et al. described above. Aqueous stock solutions of pyrithiones and silver salts (Ag₂O or AgCl) and mixtures of the two were serially diluted in microtiter plates in tryptone soy broth (TSB), pH 7.3 (bacteria and *Candida*) or Ushijima Medium (Microbiol. Immunol. 25:1109, 1981), pH 5.5 (Pyrosporum). Equal volumes of bacteria ($10^6$ cells/ml) or fungi ($10^5$ spores/ml) were added to each microtiter plate well. The plates were incubated at 35° C. for 1 to 2 days, and the minimum inhibitory concentration (MIC) of biocide was determined. The Fractional Inhibitory Concentration (FIC, concentration of biocide in an inhibitory mixture divided by the MIC of the pure biocide) of each biocide was determined, and the FIC Index ("S", the sum of the two FICs) was calculated. The type of interaction is categorized according to the magnitude of the Index, where synergistic is defined as <1, additive is approximately 1, and antagonistic is >1.

added to a metalworking fluid (MWF). An emulsion was prepared from a 5% dilution of a concentrate, consisting of mineral oil (83.5%), sulfonated hydrocarbon (10.7%), oleic acid (1.0%), triethanolamine (0.8%), methyl tallowate (3.0%), and propylene glycol ether (1.0%) and dispensed into Erlenmeyer flasks. Each sample was challenged twice over a period of 40 days with $10^7$ calls of bacteria and $10^5$ fungal TABLE 3b Interaction of Pyrithiones with Silver Salts
MIC (ppm)

| Organism | ZPT | NaPT | $Ag^{+1}$ Ion | Ratio(s) ($PT/Ag^{+1}$) | S |
|---|---|---|---|---|---|
| *Staphylococcus aureus* 27217 | | | (Source: $Ag_2O$) | | |
| | 4 | — | 0 | — | — |
| | 4 | — | 0.9-3.7 | 4.30-1.07 | 1.03-1.13 |
| | 2 | — | 7.4 | 0.27 | 0.75 |
| | 1 | — | 14.9 | 0.07 | 0.75 |
| | 0 | — | 29.8 | — | — |
| | — | 4 | 0 | — | — |
| | — | 4 | 0.9 | 4.30 | 1.03 |
| | — | 2 | 1.90-7.40 | 1.05-0.26 | 0.56-0.75 |
| | — | 0.25 | 14.9 | 0.02 | 0.56 |
| | — | 0 | 29.8 | — | — |
| *Escherichia coli* 10536 | 8 | — | 0 | — | — |
| | 2 | — | 0.9 | 2.15 | 0.75 |
| | 0.25 | — | 0.9 | 0.25 | 0.53 |
| | 0 | — | 1.9 | — | — |
| | — | 16 | 0 | — | — |
| | — | 1 | 0.9-1.9 | 1.02-0.54 | 0.19-0.31 |
| | — | 0.5 | 3.7 | 0.13 | 0.53 |
| | — | 0 | 7.4 | — | — |
| *Staphylococcus aureus* 27217 | | | (Source: $AgCl_2$) | | |
| | — | 8 | 0 | — | — |
| | — | 16 | 0.15 | 106.24 | 2.03 |
| | — | 8 | 0.3-1.2 | 26.56-6.64 | 1.03-1.13 |
| | — | 2 | 2.3 | 0.86 | 0.50 |
| | — | 0.25 | 4.7 | 0.05 | 0.53 |
| | — | 0 | 9.5 | — | — |
| *Escherichia coli* 10536 | — | 16 | 0 | — | — |
| | — | 16 | 0.8-1.5 | 21.24-10.62 | 1.04-1.08 |
| | — | 4 | 2.3 | 1.77 | 0.38 |
| | — | 1 | 2.3 | 0.44 | 0.18 |
| | — | 0.5 | 4.5 | 0.11 | 0.27 |
| | — | 0.13 | 9.79 | 0.01 | 0.53 |
| | — | 0 | 18.8 | — | — |
| *Pseudomonas aeruginosa* 9027 | — | 256 | 0 | — | — |
| | — | 256 | 0.1-3.8 | 340.00-68.00 | 1.0-2.0 |
| | — | 2-1 | 0.8 | 2.36-1.18 | 0.27-0.26 |
| | — | 4-≦1 | 1.9 | 2.12-0.53 | 0.52-≦0.56 |
| | — | 8-2 | 3.8 | 2.12-0.53 | 1.03-1.01 |
| | — | 0 | 3.8 | — | — |
| *Candida albicans* 10251 | | | (Source: $AgCl_2$) | | |
| | — | 16 | 0 | — | — |
| | — | 16 | 0.8-1.5 | 21.25-10.62 | 1.08-1.16 |
| | — | 8 | 2.3 | 3.54 | 0.74 |
| | — | 2 | 4.5 | 0.44 | 0.59 |
| | — | 0 | 9.8 | — | — |
| *Pityrosporum ovale* 1452 | — | 4 | 0 | — | — |
| | — | 2 | 0.2 | 13.28 | 0.63 |
| | — | 1 | 0.3 | 3.32 | 0.50 |
| | — | 0.5 | 0.6 | 0.83 | 0.63 |
| | — | 0 | 1.2 | — | — |

As shown in Table 3b, both of the silver salts and pyrithiones exhibited synergistic inhibition of both Gram positive and Gram negative bacteria and yeast, including the causative agent of dandruff.

Example 4

Efficacy of a Mixture of NaPT and Zn or Cu Ions in a Metalworking Fluid Emulsion A mixture of 250 ppm (v/v) of NaPT (40% active) and 10 ppm of Cu (II) ($CuSO_4 \cdot 5H_2O$) or Zn(II) ($ZnSO_4 \cdot 7H_2O$) was spores per milliliter of emulsion. The challenge consisted of seven strains of bacteria and 2 strains of fungi originally isolated from contaminated metalworking fluid: *Pseudomonas rubescens* NCIMB 12202, *Pseudomonas stutzeri* sp., *Pseudomonas fluorescens* NCIMB 12202, *Pseudomonas aeruginosa* CIMB 6749, *Pseudomonas olevorans* NCIMB 6576, *Alcaligenes faecalis* sp., *Citrobacter freundii* CIMB 12203, *Fusarium* sp., and *Cephalosporium* sp. The fluids were agitated continuously on a rotary shaker, and surviving bacteria and fungi were enumerated periodically by viable plate counts on Tryptic Soy Agar.

Figure 2:
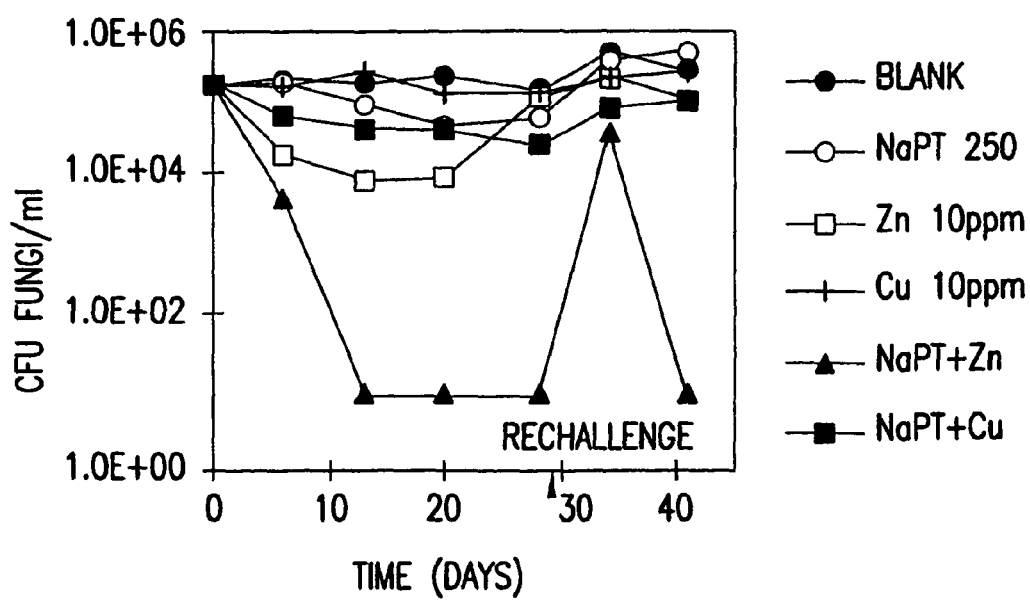
FIG. 2 is another graph showing the antifungal efficacy of sodium pyrithione plus Cu(II) or Zn(II) in a metalworking fluid.

Cu(II) (10 ppm), by itself, had little effect on reducing the growth of fungi. However, the combination of Cu(II) and NaPT exhibited an enhanced fungicidal effect (FIG. 2). As shown in FIG. 1, Cu(II), by itself, significantly reduced bacterial counts until the second challenge, whereas Cu(II)+NaPT exhibited only a slight improvement over the antibacterial efficacy of NaPT, presumably the result of the conversion of NaPT to the less water-soluble Cu salt of pyrithione.

The favorable effect of Zn(II) on NaPT efficacy was much more pronounced that the effect observed with Cu (II). Antibacterial and antifungal activities were significantly increased and persisted through the second challenge (FIGS. 1 and 2). Concentrations of 1 and 100 ppm of Zn(II) produced proportional enhancements of NaPT efficacy.

Example 5

Investigation of the Efficacy of a Mixture of Pyrithione and Metal Salts to Inhibit the Growth of Biofilms in Metalworking Fluids Experiments were conducted to investigate the efficacy of the composition of the present invention to inhibit the survival, growth, and proliferation of free-living and biofilm populations of bacteria and fungi in metalworking fluids. Test microorganisms included two bacterial species, *P. aeruginosa* 9027 and *E. coli* 8739, and a fungal isolate, *Fusarium* sp. Metalworking fluids (MWF) employed included 5% soluble oil MWF, 5% semi-synthetic MWF, or 5% synthetic MWS. For testing against bacteria, metalworking fluids were supplemented with 2% (weight-to-weight ratio (w:w)) of 5 g/L yeast extract (Difco), Metalworking fluids were supplemented with 2% (weight-to-weight (w:w)) of Tryptic Soy Broth (Difco) for fungal tests.

For each experiment, three ml of a 5% metalworking fluid was added to each of twelve, sterile, 16 mm×150 mm glass culture tubes. Each tube contained one polycarbonate disc (0.5" dia×0.125" thick) which served as a surface for biofilm attachment. For bacterial tests, *P. aeruginosa* 9027 or *E. coli* 8739 were added to the tubes to final concentrations of $10^7$ cells/ml. *Fusarium* sp. was added to the tubes to final concentrations of $10^5$ spores/ml for the fungal tests. Tubes incubated for 3 days at 28° C. and 180 rpms.

After incubation, three replicate culture tubes were randomly assigned to four treatment groups which received the following treatments: untreated control, 100 ppm or 50 PPM pyrithione (final concentration), 10 ppm Zn (II) ($ZnSO_4 \cdot 7H_2O$) (final concentration), or 100 PPM or 50 PPM pyrithione+10 ppm Zn (II) (final concentrations). After the treatments additions were performed, the culture tubes resumed incubation at 28° C., 180 rpms for an additional 4 days.

After 4 days, culture tubes were removed from the incubator and viable counts of organisms from the bulk MWF fluid and the biofilm were determined using serial dilution and drop plating techniques. For biofilms, polycarbonate discs were removed from tubes, dip-rinsed in three successive washes of de-ionized water to remove loosely attached cells, and transferred to 25 mm×150 mm culture tubes containing 10 ml of sterile, de-ionized water. Biofilms were removed from discs and resuspended by vortexing tubes for 30 seconds. Bacteria were plated on to R2A Agar plates and incubated at 37° C. Fungi were plated onto Malt Agar plates and incubated at 28° C. Mean colony forming units per ml (for bulk) and per square cm ($cm^2$) biofilm were determined for each experimental treatment.

Tables 4a-b show the results of experiments testing the efficacy of 100 PPM NaPT or 50 PPM ZPT in combination with 10 PPM Zn(II) ions against free-living and biofilm microorganisms in three metalworking fluids and in Tryptic Soy Broth (TSB). The microorganisms challenged in these tests include two bacterial isolates, *Pseudomonas aeruginosa* 9027 and *Escherichia coli* 8739, and a fungal isolate of *Fusarium* sp. In addition to displaying the microorganism, metalworking fluid type, and biocide concentrations used in each test, Tables 4a and 4b display mean number of viable free-living microorganisms per ml and of mean number of viable biofilm microorganisms per $cm^2$. Two way analysis of variance with replication of log transformed data was used to statistically test for synergy (pyrithione X zinc interaction).

TABLE 4a

Efficacy of 100 PPM Sodium Pyrithione + 10 PPM Zn (II) Against Free-Living Organisms in Metalworking Fluids.

| Microorganism | Medium | Untreated | 100 PPM NaPT | 10 PPM Zn (II) | 100 PPM NaPT 10 PPM Zn (II) |
|---|---|---|---|---|---|
| *P. aeruginosa* 9027 | 5% solub. oil | $1.1 \times 10^5$ | $8.1 \times 10^5$ | $7.2 \times 10^5$ | $2.6 \times 10^{3*}$ |
| | 5% solub. oil | $1.6 \times 10^5$ | $1.3 \times 10^6$ | $1.5 \times 10^6$ | $3.0 \times 10^{3*}$ |
| | 5% solub. oil | $1.3 \times 10^6$ | $2.1 \times 10^6$ | $1.1 \times 10^5$ | 0* |
| | 5% semisynth | $1.4 \times 10^5$ | $6.8 \times 10^4$ | $1.6 \times 10^4$ | 0* |
| | 5% semisynth | $1.2 \times 10^5$ | $1.9 \times 10^5$ | $2.4 \times 10^5$ | $3.8 \times 10^{2*}$ |
| | 5% semisynth | $8.9 \times 10^4$ | $2.3 \times 10^4$ | $8.0 \times 10^4$ | 20* |
| | 5% synthetic | $9.1 \times 10^6$ | $7.8 \times 10^6$ | $2.7 \times 10^4$ | $9.8 \times 10^4$ |
| | 5% synthetic | $3.6 \times 10^6$ | $7.0 \times 10^5$ | $8.1 \times 10^3$ | $3.5 \times 10^5$ |
| | 5% synthetic | $6.6 \times 10^6$ | $5.4 \times 10^5$ | $1.1 \times 10^6$ | $6.5 \times 10^5$ |
| *E. coil* 8739 | 10% TSB | $1.3 \times 10^9$ | $9.1 \times 10^8$ | $5.8 \times 10^8$ | $6.0 \times 10^8$ |
| | 5% solub. oil | $1.0 \times 10^8$ | $5.3 \times 10^7$ | $2.1 \times 10^4$ | $2.4 \times 10^4$ |
| | 5% semisynth. | NG | NG | NG | NG |
| | 5% semisynth. | NG | NG | NG | NG |
| | 5% synthetic | $1.8 \times 10^5$ | $3.7 \times 10^3$ | $2.2 \times 10^3$ | $3.6 \times 10^{3*}$ |
| | 5% synthetic | $1.1 \times 10^6$ | 0 | 0 | 0 |

TABLE 4a-continued

Efficacy of 100 PPM Sodium Pyrithione + 10 PPM Zn (II) Against Free-Living Organisms in Metalworking Fluids.

| | | cells/ml | | | |
|---|---|---|---|---|---|
| Microorganism | Medium | Untreated | 100 PPM NaPT | 10 PPM Zn (II) | 100 PPM NaPT 10 PPM Zn (II) |
| Fusarium sp. | 100% TSB | $2.0 \times 10^6$ | 0 | $3.4 \times 10^6$ | 0 |
| | 5% solub. oil | $4.8 \times 10^7$ | $4.2 \times 10^6$ | $2.4 \times 10^6$ | 0* |
| | 5% semisynth. | $5.1 \times 10^5$ | $2.8 \times 10^5$ | $4.6 \times 10^5$ | 0* |
| | 5% synthetic | $1.3 \times 10^7$ | $6.0 \times 10^6$ | $8.7 \times 10^6$ | 0* |

NG, no growth
*statistically significant interaction, $P < 0.05$

TABLE 4b

Efficacy of 100 PPM Sodium Pyrithione + 10 PPM Zn (II) Against Biofilm Organisms in Metalworking Fluids.

| | | cells/cm$^2$ | | | |
|---|---|---|---|---|---|
| Microorganism | Medium | Untreated | 100 PPM NaPT | 10 PPM Zn (II) | 100 PPM NaPT 10 PPM Zn (II) |
| P. aeruginosa 9027 | 5% solub. oil | $2.3 \times 10^4$ | $2.6 \times 10^4$ | $2.9 \times 10^4$ | $2.5 \times 10^{2*}$ |
| | 5% solub. oil | $6.9 \times 10^3$ | $2.6 \times 10^4$ | $1.6 \times 10^4$ | $2.4 \times 10^{2*}$ |
| | 5% solub. oil | $1.0 \times 10^4$ | $2.0 \times 10^5$ | $7.7 \times 10^3$ | 70* |
| | 5% semisynth. | $5.3 \times 10^4$ | $4.1 \times 10^4$ | $1.7 \times 10^5$ | $3.9 \times 10^2$ |
| | 5% semisynth. | $4.7 \times 10^3$ | $1.1 \times 10^3$ | $4.3 \times 10^3$ | 7* |
| | 5% semisynth. | $4.3 \times 10^3$ | $4.9 \times 10^2$ | $2.9 \times 10^3$ | 0* |
| | 5% synthetic | $3.6 \times 10^5$ | $4.1 \times 10^5$ | $3.6 \times 10^2$ | $8.9 \times 10^4$ |
| | 5% synthetic | $2.1 \times 10^5$ | $9.9 \times 10^4$ | $1.6 \times 10^3$ | $3.2 \times 10^5$ |
| | 5% synthetic | $3.0 \times 10^5$ | $2.1 \times 10^5$ | $1.4 \times 10^6$ | $8.1 \times 10^5$ |
| E. coli 8739 | 10% TSB | $1.6 \times 10^6$ | $1.4 \times 10^6$ | $6.5 \times 10^5$ | $8.6 \times 10^5$ |
| | 5% solub. oil | $2.8 \times 10^5$ | $1.6 \times 10^5$ | $1.8 \times 10^3$ | $3.3 \times 10^3$ |
| | 5% semisynth. | NG | NG | NG | NG |
| | 5% semisynth. | NG | NG | NG | NG |
| | 5% synthetic | $3.1 \times 10^4$ | 77 | 55 | $2.0 \times 10^2$ |
| | 5% synthetic | $1.6 \times 10^3$ | $1.1 \times 10^2$ | $1.1 \times 10^2$ | 26* |
| Fusarium sp. | 100% TSB | $5.4 \times 10^4$ | 96 | $3.3 \times 10^4$ | $6.8 \times 10^2$ |
| | 5% solub. oil | $6.8 \times 10^4$ | $4.6 \times 10^5$ | $4.0 \times 10^4$ | 5.3* |
| | 5% semisynth. | 23 | 18 | 27 | 0* |
| | 5% synthetic | $1.3 \times 10^5$ | $7.3 \times 10^4$ | $1.4 \times 10^5$ | $6.2 \times 10^{2*}$ |

NG, no growth
*statistically significant interaction, $P < 0.05$

As shown in Tables 4a and 4b, cultures treated with 100 PPM NaPT alone or with 10 PPM Zn (II) alone display usually less than an order of magnitude fewer viable free-living and biofilm P. aeruginosa and Fusarium sp. cells compared to untreated cultures in all three metalworking fluids. One exception to this, however, includes the effectiveness of treatment with 10 PPM Zn (II) alone against P. aeruginosa in this synthetic fluid which decreased viable counts in treated cultures by about two orders of magnitude compared to untreated controls. Also notable, E. coli was sensitive to 100 PPM NaPT alone in this synthetic fluid and to 10 PPM Zn (II) alone in these soluble oil and synthetic metalworking fluids. The effectiveness of biocides are known to be influenced by the specific formulations of metalworking fluids and may vary within and between metalworking fluid types.

In contrast to the ineffectiveness of 100 PPM NaPT or 10 PPM Zn (II) alone against P. aeruginosa and Fusarium, cultures treated with a combination of 100 PPM NaPT and 10 PPM Zn (II) showed from 1.5 up to 6.0 orders of magnitude fewer viable counts of free-living and biofilm cells of P. aeruginosa and Fusarium than untreated control cultures. An analysis of variance indicated the presence of synergistic antimicrobial activities (P<0.05) between 100 PPM NaPT and 10 PPM Zn (II) ions against P. aeruginosa free-living cells and biofilm cells in soluble oil and semi-synthetic metalworking fluids and against free-living and biofilm Fusarium sp. in soluble oil, semi-synthetic, and synthetic metalworking fluids.

Table 5 shows the mean numbers of viable P. aeruginosa biofilm cells present on different types of growth surfaces when grown for three days in the different types of metalworking fluids. These results suggest that soluble oil and synthetic metalworking fluids support biofilms of greater cell density than semi-synthetic fluids. Furthermore, rubber surfaces tend to allow greater biofilm growth than stainless steel or polycarbonate surfaces.

TABLE 5

Mean cfu/cm$^2$ of P. aeruginosa when grown on selected surface compositions

| | Metalworking Fluid Type | | |
|---|---|---|---|
| Surface | Soluble Oil | Semi-Synthetic | Synthetic |
| Stainless Steel | $2.8 \times 10^4$ | $6.9 \times 10^3$ | $4.6 \times 10^6$ |
| Rubber | $2.8 \times 10^7$ | $1.2 \times 10^6$ | $1.6 \times 10^7$ |
| Polycarbonate | $6.1 \times 10^6$ | $5.6 \times 10^3$ | $6.5 \times 10^5$ |

Microorganisms are known to adhere to and/or form biofilms on all types of surfaces. Therefore, additional experiments were conducted to investigate the efficacy of the composition of the present invention to inhibit the survival, growth, and proliferation of free-living and biofilm bacteria attached to different surface types in metalworking fluids. As described in the previous experiments, three ml of a 5% soluble oil metalworking fluid was added to sterile, 16 mm×150 mm glass culture tubes. Tubes contained polycarbonate disc (0.5" dia×0.125" thick), neoprene rubber discs (0.5" dia×0.25" thick), or steel washers (0.4" outer diameter, 0.2 inner diameter, X 0.03" thick). *P. aeruginosa* 9027 was added to the tubes to final concentrations of $10^7$ cells/ml and the tubes incubated for 3 days at 28° C. and 180 rpm. For each surface type (polycarbonate, rubber or steel), three replicate tubes were randomly assigned to one of four treatment groups: untreated control, 100 ppm sodium pyrithione (final concentration), 2.5 ppm Zn(II) (ZnSO$_4$.7H$_2$O) (final concentration), or 100 PPM sodium pyrithione+2.5 ppm Zn(II) (final concentrations). Culture tubes resumed incubation at 28° C., 180 rpms for an additional 4 days. Sampling of bulk fluid and biofilm organisms is as described above. Results of this experiment are shown in Tables 6a and 6b.

surfaces. The efficacy of the combination of 100 PPM NaPT and 2.5 PPM Zn(II) ions against *P. aeruginosa* biofilms grown on various surface types is similar to that of the combination of 100 PPM NaPT and 10 PPM Zn(II) ions against biofilms grown on polycarbonate. This suggests that utilizing 2.5 PPM Zn(II) ions with 100 PPM NaPT will be effective at disinfecting free-living cells and biofilms grown on broad range of surface types and that the addition of 2.5 PPM Zn(II) to 100 PPM NaPT is as about efficacious as adding 10 PPM Zn (II) ions.

Similar experiments were undertaken to test the efficacy of a combination of 100 PPM NaPT and 2.5 PPM Zn(II) against free-living and biofilm cells of a bacterial consortia made up of several species of bacteria often found in contaminated metalworking fluids. These bacteria included *Pseudomonas aeruginosa* 9027, *Pseudomonas putida* sp., *Pseudomonas fluorescens* NICMB 12201, *Pseudomonas rubescens* NICMB 12202, *Escherichia coli* 8379, *Citrobacter freundii* NCIMB 6576, and *Alcaligenes faecalis* sp. These experiments were conducted in all three types of metalworking fluids and biofilms were grown on polycarbonate, rubber, and stainless steel surfaces. The results of these experiments indi- TABLE 6a Efficacy of Sodium Pyrithione and Zinc Combination Against Free-Living *P. aeruginosa* in the Bulk Fluid of 5% Soluble Oil Metalworking Fluid.

| | | cells/ml | | | |
|---|---|---|---|---|---|
| Organism | Surface | Untreated | 100 PPM NaPT | 2.5 PPM Zn(II) | 100 PPM NaPT 2.5 PPM Zn(II) |
| *P. aeruginosa* 9027 | Polycarbonate | $3.7 \times 10^4$ | $4.9 \times 10^5$ | $3.1 \times 10^5$ | $2.6 \times 10^3$* |
| | Rubber | $2.0 \times 10^6$ | 50 | $8.0 \times 10^5$ | 0* |
| | Steel | $6.1 \times 10^5$ | $3.5 \times 10^6$ | $2.1 \times 10^6$ | $2.0 \times 10^2$* |

*statistically significant interaction, P < 0.05

TABLE 6b

Efficacy of Sodium Pyrithione and Zinc Combination Against *P. aeruginosa* in the Biofilm of 5% Soluble Oil Metalworking Fluid.

| | | cells/cm$^2$ | | | |
|---|---|---|---|---|---|
| Organism | Surface | Untreated | 100 PPM NaPT | 2.5 PPM Zn(II) | 100 PPM NaPT 2.5 PPM Zn (II) |
| *P. aeruginosa* 9027 | Polycarbonate | $1.3 \times 10^4$ | $2.8 \times 10^4$ | $4.7 \times 10^4$ | $9.7 \times 10^2$* |
| | Rubber | $3.0 \times 10^7$ | $5.3 \times 10^2$ | $2.4 \times 10^7$ | $8.0 \times 10^2$ |
| | Steel | $4.2 \times 10^3$ | $1.1 \times 10^5$ | $1.5 \times 10^4$ | 83* |

*statistically significant interaction, P < 0.05

The results shown in Tables 6a and 6b show that cultures treated with the combination of 100 PPM NaPT and 2.5 PPM Zn (II) had fewer viable free-living cells, and fewer viable biofilms cells when grown on polycarbonate, rubber, or steel, respectively, than untreated cultures. The efficacy of the mixture of 100 PPM NaPT and 2.5 PPM Zn(II) also demonstrated a much greater efficacy against free-living and biofilm bacteria on polycarbonate and steel than NaPT or Zn(II) ions alone. An analysis of variance detected the presence of synergistic antimicrobial activities (interaction; P<0.05) between 100 PPM NaPT and 2.5 PPM Zn(II) against free-living and biofilm cells in all cases, excepting biofilms grown on rubber cate that in soluble oil and semi-synthetic fluids, treatment of cultures with the combination of 100 PPM NaPT and 2.5 PPM Zn(II) reduced viable free-living consortia cells by about five orders of magnitude and reduced viable biofilm cells by two orders of magnitude.

The efficacy of combinations of 100 ppm NaPT and 10 ppm of selected other metal ions against *P. aeruginosa* free-living and biofilms cells are shown in Table 7a, 7b, and 7c. These experiments were conducted in three types of metalworking fluids and biofilms were grown on polycarbonate surfaces. Tables 7a, 7b, and 7c display the average number of viable free-living cells per ml and biofilm cells per square centimeter.

TABLE 7a

Efficacy of 100 PPM Sodium Pyrithione and Various Metal Ions Against Free-Living and Biofilm *P. aeruginosa* in 5% Soluble Oil Metalworking Fluid.

| Untreated | NaPT 100 PPM + Cu (II) 10 PPM | NaPT 100 PPM + Fe (II) 10 PPM | NaPT 100 PPM + Mn (II) 10 PPM | NaPT 100 PPM + Mg (II) 10 PPM | NaPT 100 PPM + Na 10 PPM | NaPT 100 PPM + Co (II) 10 PPM |
|---|---|---|---|---|---|---|
| Free-Living Cells/ml ||||||||
| $4.0 \times 10^5$ | $2.4 \times 10^6$ | $2.1 \times 10^5$ | $1.2 \times 10^6$ | $4.4 \times 10^6$ | $9.1 \times 10^4$ | $1.0 \times 10^6$ |
| Biofilm Cells/cm² ||||||||
| $1.0 \times 10^4$ | $6.1 \times 10^4$ | $9.3 \times 10^6$ | $6.6 \times 10^6$ | $1.2 \times 10^7$ | $4.6 \times 10^6$ | $5.9 \times 10^6$ |

TABLE 7b

Efficacy of 100 PPM Sodium Pyrithione and Various Metal Ions Against Free-Living and Biofilm *P. aeruginosa* in 5% Semi-synthetic Metalworking Fluid.

| Untreated | NaPT 100 PPM + Cu (II) 10 PPM | NaPT 100 PPM + Fe (II) 10 PPM | NaPT 100 PPM + Mn (II) 10 PPM | NaPT 100 PPM + Mg (II) 10 PPM | NaPT 100 PPM + Na 10 PPM | NaPT 100 PPM + Co (II) 10 PPM |
|---|---|---|---|---|---|---|
| Free-Living Cells/ml ||||||||
| $2.7 \times 10^4$ | $3.7 \times 10^4$ | $1.3 \times 10^5$ | $3.9 \times 10^3$ | $3.4 \times 10^5$ | $3.3 \times 10^3$ | $1.5 \times 10^5$ |
| Biofilm Cells/cm² ||||||||
| $1.5 \times 10^5$ | $5.3 \times 10^5$ | $4.3 \times 10^5$ | $1.1 \times 10^2$ | $2.3 \times 10^5$ | $2.5 \times 10^4$ | $4.6 \times 10^4$ |

TABLE 7c

Efficacy of 100 PPM Sodium Pyrithione and Various Metal Ions Against Free-Living and Biofilm *P. aeruginosa* in 5% Synthetic Metalworking Fluid.

| Untreated | NaPT 100 PPM + Cu (II) 10 PPM | NaPT 100 PPM + Fe (II) 10 PPM | NaPT 100 PPM + Mn (II) 10 PPM | NaPT 100 PPM + Mg (II) 10 PPM | NaPT 100 PPM + Na 10 PPM | NaPT 100 PPM + Co (II) 10 PPM |
|---|---|---|---|---|---|---|
| Free-Living Cells/ml ||||||||
| $3.8 \times 10^6$ | $2.6 \times 10^5$ | $4.9 \times 10^6$ | $9.6 \times 10^2$ | $6.6 \times 10^5$ | $3.0 \times 10^4$ | $7.7 \times 10^5$ |
| Biofilm Cells/cm² ||||||||
| $4.0 \times 10^5$ | $2.4 \times 10^3$ | $2.6 \times 10^6$ | $1.1 \times 10^3$ | $7.1 \times 10^3$ | $7.9 \times 10^3$ | $1.1 \times 10^4$ |

The results of these experiments show that, in soluble oil and semi-synthetic fluids, cultures treated with 100 ppm NaPT and 10 ppm of Cu(II), Fe(II), Mg(II), Na, or Co(II) contain about the same or higher numbers of viable free-living and biofilm cells as untreated cultures. The combination of 100 ppm NaPT and 10 ppm Mn(II), however, reduces viable biofilm cell counts by three orders of magnitude. In synthetic fluids, cultures treated with 100 ppm NaPT and 10 ppm of any metal ion other than Fe(II) displayed at two orders of magnitude less viable biofilm cells than untreated culture. Because 100 ppm NaOM alone has little effectiveness against *P. aeruginosa* biofilm cells in metalworking fluids, these results suggest that the addition of a broad range of metal ions to 100 ppm NaPT can increase the efficacy of NaPT in synthetic metalworking fluids.

Example 6

Effect of $Zn^{2+}$ on Efficacy of Zinc Pyrithione in a Soluble Oil Metalworking Fluid The novel effects of Zn ion on pyrithione antimicrobial activity is illustrated in this example. In previous examples, metalworking fluids were dosed with a mixture of 100 ppm of NaPT and 10 ppm of $Zn^{2+}$. The theoretical amount of ZPT generated in the fluid would be 48.5 ppm. In this example, 50 ppm of added ZPT was supplemented with an additional 10 ppm of $Zn^{2+}$ and compared with the NaPT/Zn mixture.

A metalworking fluid was amended with ZPT and Zn ion and challenged with seven cultures of bacteria and two cultures of fungi as described previously. For comparison, samples of fluid amended with 50 ppm of the copper salt of pyrithione (CuPT) and 10 ppm of $Zn^{2+}$ were also tested. The results are shown in Table 8 expressed as CFU/ml.

TABLE 8

Effect of $Zn^{2+}$ on Efficacy of Zinc Pyrithione in a Soluble Oil Metalworking Fluid.

| DAY | Blank | 10 ppm Zn | 100 ppm NaPT + 10 ppm Zn | 50 ppm ZPT | 50 ppm ZPT + 10 ppm Zn | 50 ppm CuPT | 50 ppm CuPT + 10 ppm Zn |
|---|---|---|---|---|---|---|---|
| BACTERIA (cfu/ml) | | | | | | | |
| 0 | $3.2 \times 10^7$ | $3.2 \times 10^7$ | $3.2 \times 10^7$ | $3.2 \times 10^7$ | $3.2 \times 10^7$ | $3.2 \times 10^7$ | $3.2 \times 10^7$ |
| 6 | $2.0 \times 10^7$ | $4.7 \times 10^6$ | $1.5 \times 10^3$ | 1000 | 10 | $1.5 \times 10^7$ | 10 |
| 13 | $2.1 \times 10^7$ | $1.1 \times 10^7$ | $2.3 \times 10^4$ | 4400 | 10 | $9.7 \times 10^6$ | 10 |
| 20 | $2.3 \times 10^7$ | $7.2 \times 10^6$ | $3.0 \times 10^4$ | 7700 | 10 | $1.9 \times 10^6$ | 10 |
| FUNGI (cfu/ml) | | | | | | | |
| 0 | $2.4 \times 10^5$ | $2.4 \times 10^5$ | $2.4 \times 10^5$ | $2.4 \times 10^5$ | $2.4 \times 10^5$ | $2.4 \times 10^5$ | $2.4 \times 10^5$ |
| 6 | $1.7 \times 10^5$ | $7.5 \times 10^4$ | $1.5 \times 10^4$ | 1000 | 5800 | 1000 | 690 |
| 13 | $2.2 \times 10^5$ | $3.5 \times 10^4$ | 10 | 10 | 90 | 680 | 830 |
| 20 | $1.5 \times 10^5$ | $2.2 \times 10^4$ | 100 | 10 | 10 | 370 | 880 |

As shown in Table 8, the bacterial data showed that Zn (II) ions significantly improved the activities of ZPT beyond the level expected from the amount of ZPT generated in situ from added Zn and NaPT. Similar results were obtained with CuPT. The phenomenon was not evident in the fungal data: ZPT and CuPT, alone were strongly fungicidal. Accordingly, this data suggests that Zn ion unexpectedly enhances the activities of pyrithione biocides in general.

Example 7

Efficacy of 100 PPM NaPT And 15 PPM Zn (II) Ions Against Free-Living And Biofilm Associated Microorganisms in Simulated Metalworking Fluid System A five gallon, glass aquarium tank was disinfected with bleach and set up to simulate a recirculating metalworking fluid system. An aquarium pump was attached to the tank as a means of recirculating the fluid through the tank. To provide sampling surfaces for biofilm growth, stainless steel washer coupons (surface area, 1.2 $cm^2$) and polycarbonate disc coupons (surface area, 3.8 $cm^2$) were attached to glass slide coupon holders with double stick carpet tape. The coupon holders were then attached by carpet tape to the floor and sides of the tank. Two steel and two polycarbonate coupons were placed on each holder. 12.5 liters of dilute (1:20) semi-synthetic metalworking fluid was added to the tank. Bacteria were added to a final concentration of $10^6$ bacteria/ml. The bacterial inoculum consisted of an equal number of cells from *Pseudomonas aeruginosa* 9027, *Escherichia coli* 8739, *Pseudomonas fluorescens* 12201, *Pseudomonas rubescens* 12202, and *Pseudomonas putida*. Fungal spores were added to the tank to final concentrations of $10^4$ spores/ml. Fungal additions consisted of an equal number of spores from *Fusarium* sp. and *Cephalosporium* sp. metalworking fluid field isolates. Bacterial and fungal additions were repeated three times per week.

The tank was recirculated at room temperature (23° C.±2° C.) for 19 days and then sampled for initial bacterial and fungal densities in the bulk fluid and biofilm. For the bulk fluid, samples from the tank were serially diluted (1:10) in sterile, de-ionized water and spread plated for bacterial and fungal counts on Tryptic Soy Agar plus 90 PPM cycloheximide and Malt Agar plus 900 PPM streptomycin plus 550 PPM Penicillin G, respectively. For biofilm samples, coupons holders were removed from the bottom and sides of the tank. Coupons were removed from the holders, dip rinsed in sterile water, and transferred to 25 mm×150 mm glass disposal culture tubes containing 10 ml of sterile, de-ionized water. Biofilms were liberated from the coupons and resuspended by vortexing tubes at maximum speed for 30 seconds. Resuspended biofilms were then serially diluted and plated for bacteria and fungal counts as described for bulk fluid samples. 0.5 ml of slime material from the sides for the tank at the fluid-air interface were sampled by a sterile, needless syringe and resuspended in sterile, de-ionized water and by vortexing. Counts of bacterial and fungi in the slime samples were also determined as described previously for bulk fluid samples. Plates were incubated at 28° C. for two to three days and then scored for colony forming units. For biofilm samples, excepting the slime material, colony forming units per ml were converted to colony forming units per $cm^2$.

NaPT and Zn (II) ions ($ZnSO_4 \cdot 7H_2O$) were added to the tank to final concentrations of 100 PPM and 15 PPM, respectively. The tank was allowed to recirculate for four days. At day 4 after NaPT and Zn (II) treatment, bacteria and fungal densities in the bulk fluid and biofilm were determined as described above for the initial sampling. Table 9 shows the results of this experiment.

TABLE 9

The Efficacy Of 100 PPM NaPT And 15 PPM Zn (II) Ions Against Free-Living And Biofilm Associated Microorganisms In Simulated Metalworking Fluid System.

| | Pre-treatment | | Post-Treatment | |
|---|---|---|---|---|
| Sample | Bacteria/ml | Fungi/ml | Bacteria/ml | Fungi/ml |
| Bulk Fluid | | | | |
| 1 | $1.3 \times 10^7$ | $7.0 \times 10^3$ | $1.3 \times 10^4$ | 0 |
| 2 | $1.2 \times 10^7$ | $6.0 \times 10^3$ | $1.4 \times 10^4$ | 0 |
| Biofilm tank floor | | | | |
| Stainless steel | | | | |
| 1 | $4.4 \times 10^6$ | $9.2 \times 10^4$ | $7.0 \times 10^3$ | 10 |
| 2 | $2.0 \times 10^6$ | $1.3 \times 10^5$ | $1.2 \times 10^4$ | 0 |

TABLE 9-continued

The Efficacy Of 100 PPM NaPT And 15 PPM Zn (II) Ions
Against Free-Living And Biofilm Associated
Microorganisms In Simulated Metalworking Fluid System.

| | Pre-treatment | | Post-Treatment | |
|---|---|---|---|---|
| Sample | Bacteria/ml | Fungi/ml | Bacteria/ml | Fungi/ml |
| Polycarbonate | | | | |
| 1 | $5.6 \times 10^6$ | $1.5 \times 10^5$ | $4.0 \times 10^4$ | 0 |
| 2 | $2.4 \times 10^6$ | $1.3 \times 10^5$ | $5.6 \times 10^4$ | 0 |
| | | Biofilm tank side | | |
| Stainless steel | | | | |
| 1 | $2.3 \times 10^6$ | $1.1 \times 10^4$ | $1.0 \times 10^4$ | 0 |
| 2 | $2.3 \times 10^6$ | $3.0 \times 10^4$ | $2.4 \times 10^4$ | 0 |
| Polycarbonate | | | | |
| 1 | $2.8 \times 10^6$ | $2.0 \times 10^4$ | $2.8 \times 10^3$ | 0 |
| 2 | $2.0 \times 10^6$ | $1.6 \times 10^4$ | $2.2 \times 10^3$ | 0 |
| | | Splash area slime tank side | | |
| 1 | $1.9 \times 10^5$ | $1.0 \times 10^4$ | $4.8 \times 10^3$ | 30 |

As shown in Table 9, treatment of the tank with 100 PPM NaPT and 15 PPM Zn (II) ions resulted in a 1000-fold reduction in bacterial numbers and a 6000-fold decrease in fungal numbers in the bulk fluid. No fungal could be detected in the bulk fluid. Furthermore, treatment reduced biofilm bacteria counts by about 100 to 1000-fold and biofilm fungal counts by 10,000 to 100,000-fold. Nearly no fungi could be detect in the submerged biofilms or in the slime material at the air-fluid interface. This data suggest that the composition of the present invention is operative under conditions similar to those found in the field.

Example 8

Efficacy of Various Mixtures of NaPT and Zn(II) Ions Against Microorganisms in Metalworking Fluids Sterile, glass, disposable culture tubes (16 mm×150 mm) containing three ml of 5% metalworking fluid were set up for each of the following metalworking fluid types: soluble oil, semi-synthetic, and synthetic. To each tube, bacteria were added to a final concentration of $10^7$ bacteria/ml. The bacterial inoculum consisted of an equal number of cells from *Pseudomonas aeruginosa* 9027, *Escherichia coli* 8739, *Pseudomonas fluorescens* 12201, *Pseudomonas rubescens* 12202, and *Pseudomonas putida*. Fungal spores were added to each tube to final concentrations of $10^5$ spores/ml. Fungal additions consisted of an equal number of spores from *Fusarium* sp. and *Cephalosporium* sp. metalworking fluid field isolates. Tubes were incubated 28° C. and 180 rpms for seven days.

Pretreatment cell densities of bacteria and fungi were determined by serially diluting fluid samples (1:10) in sterile, de-ionized water and spread plating the dilutions for bacterial and fungal counts on Tryptic Soy Agar plus 90 PPM cycloheximide and Malt Agar plus 900 PPM streptomycin plus 550 PPM Penicillin G, respectively. Plates were incubated at 28° C. for two to three days and then scored for colony forming units (cfu). After initial sampling, tubes received the following biocide treatments. For each fluid type, an untreated control tube containing no NaPT or Zn(II) ions was established. NaPT alone was added to construct several NaPT control tubes with no zinc present. Similarly, Zn (II) ions ($ZnSO_4.7H_2O$) alone were used to set up several zinc control tubes containing no NaPT. Test treatment tubes consisting of mixtures of NaPT and Zn (II) ions were also constructed. Tubes resumed incubation at 28° C. and 180 rpms and were sampled for bacterial and fungal densities on days 1, 2, 4, or 7 post-treatment. Experimental results are shown in Tables 10a and 10b.

TABLE 10a

Efficacy of Various Mixtures of NaPT and Zinc Ions
Against Bacteria in 5% Metalworking Fluid.

| NaPT PPM | Zn (II) PPM | Ratio Zn:PT | Bacteria/ml | | | |
|---|---|---|---|---|---|---|
| | | | Day 1 | Day 2 | Day 4 | Day 7 |
| | | Soluble oil | | | | |
| 0 | 0 | — | $4.0 \times 10^5$ | $2.0 \times 10^5$ | ND | $2.0 \times 10^4$ |
| 0 | 0 | — | $6.1 \times 10^6$ | ND | $3.9 \times 10^6$ | ND |
| 0 | 10 | — | $5.0 \times 10^5$ | $1.7 \times 10^5$ | ND | $2.0 \times 10^5$ |
| 0 | 20 | — | $1.4 \times 10^5$ | $1.6 \times 10^5$ | ND | $2.0 \times 10^4$ |
| 0 | 30 | — | $3.0 \times 10^4$ | $7.5 \times 10^4$ | ND | $2.0 \times 10^3$ |
| 0 | 100 | — | $2.0 \times 10^6$ | ND | 0 | ND |
| 0 | 500 | — | 0 | ND | 0 | ND |
| 0 | 1000 | — | 0 | ND | 0 | ND |
| 0 | 5000 | — | 0 | ND | 0 | ND |
| 100 | 0 | — | $2.4 \times 10^5$ | $6.0 \times 10^3$ | ND | $2.0 \times 10^4$ |
| 100 | 0 | — | $5.9 \times 10^6$ | ND | $1.5 \times 10^6$ | ND |
| 100 | 10 | 1:10 | $1.2 \times 10^{4}$*** | 0*** | ND | 0*** |
| 100 | 20 | 1:5 | $5.5 \times 10^{4}$* | 0*** | ND | 0*** |
| 100 | 30 | 1:3.3 | $1.0 \times 10^{3}$*** | 0*** | ND | 0*** |
| 100 | 100 | 1:1 | 0*** | ND | 0 | ND |
| 100 | 500 | 5:1 | 0 | ND | 0 | ND |
| 100 | 1000 | 10:1 | 0 | ND | 0 | ND |
| 100 | 5000 | 50:1 | 0 | ND | 0 | ND |
| 300 | 0 | — | $7.1 \times 10^4$ | $9.0 \times 10^3$ | ND | 0 |
| 300 | 10 | 1:30 | $1.3 \times 10^4$ | 560*** | ND | 0 |
| 300 | 20 | 1:25 | $3.0 \times 10^3$ | 0*** | ND | 0 |
| 300 | 30 | 1:10 | $2.9 \times 10^4$ | $1.4 \times 10^{3}$* | ND | 0 |
| 500 | 0 | — | ND | 450 | ND | 0 |
| 500 | 10 | 1:50 | $4.0 \times 10^5$ | 260* | ND | 0 |

TABLE 10a-continued

Efficacy of Various Mixtures of NaPT and Zinc Ions Against Bacteria in 5% Metalworking Fluid.

| NaPT PPM | Zn (II) PPM | Ratio Zn:PT | Bacteria/ml Day 1 | Day 2 | Day 4 | Day 7 |
|---|---|---|---|---|---|---|
| 500 | 20 | 1:25 | $1.1 \times 10^4$ | 420 | ND | 0 |
| 500 | 30 | 1:16.7 | $3.2 \times 10^4$ | 610 | ND | 0 |
| Semi-synthetic | | | | | | |
| 0 | 0 | — | $1.9 \times 10^3$ | $1.2 \times 10^5$ | ND | $4.0 \times 10^3$ |
| 0 | 0 | — | $2.6 \times 10^6$ | ND | $8.0 \times 10^4$ | ND |
| 0 | 10 | — | 170 | $3.2 \times 10^5$ | ND | $4.8 \times 10^4$ |
| 0 | 20 | — | $1.5 \times 10^5$ | $1.4 \times 10^4$ | ND | $4.0 \times 10^3$ |
| 0 | 30 | — | $1.7 \times 10^3$ | $1.5 \times 10^5$ | ND | $1.3 \times 10^5$ |
| 0 | 100 | — | $4.9 \times 10^4$ | ND | $5.7 \times 10^4$ | ND |
| 0 | 500 | — | $9.5 \times 10^4$ | ND | $1.1 \times 10^5$ | ND |
| 0 | 1000 | — | 0 | ND | 0 | ND |
| 0 | 5000 | — | 0 | ND | 0 | ND |
| 100 | 0 | — | $1.8 \times 10^5$ | $1.9 \times 10^5$ | ND | 510 |
| 100 | 0 | — | $1.7 \times 10^4$ | ND | $1.2 \times 10^4$ | ND |
| 100 | 10 | 1:10 | 200 | 0*** | ND | 0*** |
| 100 | 20 | 1:5 | $4.7 \times 10^4$ | 150*** | ND | 0*** |
| 100 | 30 | 1:3.3 | $1.1 \times 10^4$ | 100*** | ND | 0*** |
| 100 | 100 | 1:1 | 0*** | ND | 0*** | ND |
| 100 | 500 | 5:1 | 0*** | ND | 0*** | ND |
| 100 | 1000 | 10:1 | 0 | ND | 0*** | ND |
| 100 | 5000 | 50:1 | 0 | ND | 0 | ND |
| 300 | 0 | — | $1.2 \times 10^5$ | 0 | ND | 0 |
| 300 | 10 | 1:30 | $2.0 \times 10^4$ | 0* | ND | 0*** |
| 300 | 20 | 1:15 | $1.9 \times 10^4$ | 0 | ND | 0 |
| 300 | 30 | 1:10 | $1.6 \times 10^4$ | 0* | ND | 0*** |
| 500 | 0 | — | ND | 0 | ND | 0 |
| 500 | 10 | 1:50 | ND | 0* | ND | 0*** |
| 500 | 20 | 1:25 | $2.7 \times 10^4$ | 0 | ND | 0 |
| 500 | 30 | 1:16.7 | $1.6 \times 10^4$ | 0* | ND | 0*** |
| Synthetic | | | | | | |
| 0 | 0 | — | $5.3 \times 10^6$ | $1.2 \times 10^5$ | ND | $1.3 \times 10^4$ |
| 0 | 0 | — | $8.4 \times 10^6$ | ND | $3.5 \times 10^6$ | ND |
| 0 | 10 | — | 30 | 0 | ND | 0 |
| 0 | 20 | — | 190 | 0 | ND | 0 |
| 0 | 30 | — | 0 | 0 | ND | 0 |
| 0 | 100 | — | 0 | ND | 0 | ND |
| 0 | 500 | — | 0 | ND | 0 | ND |
| 0 | 1000 | — | 0 | ND | 0 | ND |
| 0 | 5000 | — | 0 | ND | 0 | ND |
| 100 | 0 | — | $2.9 \times 10^6$ | $1.7 \times 10^5$ | ND | $1.5 \times 10^4$ |
| 100 | 0 | — | $2.1 \times 10^6$ | ND | $2.0 \times 10^5$ | ND |
| 100 | 10 | 1:10 | $2.2 \times 10^4$ | 0 | ND | 0 |
| 100 | 20 | 1:5 | $3.0 \times 10^3$ | 0 | ND | 0 |
| 100 | 30 | 1:3.3 | 0 | 0 | ND | 0 |
| 100 | 100 | 1:1 | 0 | ND | 0 | ND |
| 100 | 500 | 5:1 | 0 | ND | 0 | ND |
| 100 | 1000 | 10:1 | 0 | ND | 0 | ND |
| 100 | 5000 | 50:1 | 0 | ND | 0 | ND |
| 300 | 0 | — | $5.0 \times 10^4$ | $4.0 \times 10^3$ | ND | 0 |
| 300 | 10 | 1:30 | 80 | 0 | ND | 0 |
| 300 | 20 | 1:15 | 250 | 0 | ND | 0 |
| 300 | 30 | 1:10 | $1.8 \times 10^4$ | 20 | ND | 0 |
| 500 | 0 | — | $1.2 \times 10^5$ | $1.0 \times 10^3$ | ND | 50 |
| 500 | 10 | 1:50 | 0 | 0 | ND | 0 |
| 500 | 20 | 1:25 | 810 | 0 | ND | 0 |
| 500 | 30 | 1:16.7 | 360 | 0 | ND | 0 |

ND, not determined.

TABLE 10b

Efficacy of Various Mixtures of NaPT and Zinc Ions Against Fungi in 5% Metalworking Fluid.

| NaPT PPM | Zn(II) PPM | Ratio Zn:PT | Day 1 | Day 2 | Day 4 | Day 7 |
|---|---|---|---|---|---|---|
| | | | Soluble oil | | | |
| 0 | 0 | — | $3.0 \times 10^4$ | $6.0 \times 10^4$ | ND | $4.0 \times 10^4$ |
| 0 | 0 | — | $4.1 \times 10^4$ | ND | $3.9 \times 10^4$ | ND |
| 0 | 10 | — | $3.3 \times 10^4$ | $4.2 \times 10^4$ | ND | $3.3 \times 10^4$ |
| 0 | 20 | — | $4.0 \times 10^4$ | $5.6 \times 10^4$ | ND | $2.3 \times 10^4$ |
| 0 | 30 | — | $1.8 \times 10^4$ | $5.0 \times 10^3$ | ND | $1.9 \times 10^4$ |
| 0 | 100 | — | $2.7 \times 10^4$ | ND | $7.5 \times 10^2$ | ND |
| 0 | 500 | — | $3.5 \times 10^2$ | ND | 0 | ND |
| 0 | 1000 | — | $5.5 \times 10^2$ | ND | 0 | ND |
| 0 | 5000 | — | $7.7 \times 10^2$ | ND | 0 | ND |
| 100 | 0 | — | $3.2 \times 10^4$ | $2.9 \times 10^4$ | ND | $1.5 \times 10^4$ |
| 100 | 0 | — | $3.6 \times 10^4$ | ND | $2.9 \times 10^4$ | ND |
| 100 | 10 | 1:10 | $2.3 \times 10^{4}$* | 610*** | ND | 0*** |
| 100 | 20 | 1:5 | $2.0 \times 10^{4}$* | 560*** | ND | 0*** |
| 100 | 30 | 1:3.3 | $1.6 \times 10^{4}$* | 20*** | ND | 0*** |
| 100 | 100 | 1:1 | $1.1 \times 10^{4}$* | ND | 0*** | ND |
| 100 | 500 | 5:1 | 0*** | ND | 0 | ND |
| 100 | 1000 | 10:1 | 0*** | ND | 0 | ND |
| 100 | 5000 | 50:1 | 0*** | ND | 0 | ND |
| 300 | 0 | — | $1.7 \times 10^4$ | $1.0 \times 10^4$ | ND | 560 |
| 300 | 10 | 1:30 | $2.5 \times 10^4$ | $1.5 \times 10^4$ | ND | 0*** |
| 300 | 20 | 1:15 | $2.4 \times 10^4$ | $2.0 \times 10^{3}$* | ND | 0*** |
| 300 | 30 | 1:10 | $3.5 \times 10^4$ | $2.0 \times 10^4$ | ND | 0*** |
| 500 | 0 | — | $1.9 \times 10^4$ | $2.8 \times 10^4$ | ND | 610 |
| 500 | 10 | 1:50 | $2.4 \times 10^4$ | $1.3 \times 10^{4}$* | ND | 0*** |
| 500 | 20 | 1:25 | $2.9 \times 10^4$ | $3.5 \times 10^4$ | ND | 0*** |
| 500 | 30 | 1:16.7 | $1.6 \times 10^4$ | $1.5 \times 10^3$ | ND | 0*** |
| | | | Semi-synthetic | | | |
| 0 | 0 | — | $1.0 \times 10^4$ | $1.4 \times 10^4$ | ND | $4.0 \times 10^3$ |
| 0 | 0 | — | $2.4 \times 10^4$ | ND | $1.4 \times 10^4$ | ND |
| 0 | 10 | — | $1.0 \times 10^4$ | $5.0 \times 10^3$ | ND | $4.8 \times 10^2$ |
| 0 | 20 | — | $1.2 \times 10^4$ | $1.6 \times 10^4$ | ND | $4.0 \times 10^3$ |
| 0 | 30 | — | $1.2 \times 10^4$ | $1.5 \times 10^4$ | ND | $1.3 \times 10^3$ |
| 0 | 100 | — | $3.3 \times 10^4$ | ND | $1.1 \times 10^4$ | ND |
| 0 | 500 | — | $4.4 \times 10^4$ | ND | $2.0 \times 10^4$ | ND |
| 0 | 1000 | — | $4.1 \times 10^4$ | ND | $1.0 \times 10^4$ | ND |
| 0 | 5000 | — | 0 | ND | 0 | ND |
| 100 | 0 | — | $1.1 \times 10^4$ | $1.3 \times 10^3$ | ND | 0 |
| 100 | 0 | — | $2.0 \times 10^4$ | ND | $1.0 \times 10^4$ | ND |
| 100 | 10 | 1:10 | 200*** | 0*** | ND | 0 |
| 100 | 20 | 1:5 | 70*** | 0*** | ND | 0 |
| 100 | 30 | 1:3.3 | 150*** | 0*** | ND | 0 |
| 100 | 100 | 1:1 | 40*** | ND | 0*** | ND |
| 100 | 500 | 5:1 | $2.2 \times 10^{2}$*** | ND | 0*** | ND |
| 100 | 1000 | 10:1 | 0*** | ND | 0 | ND |
| 100 | 5000 | 50:1 | 0 | ND | 0 | ND |
| 300 | 0 | — | $3.0 \times 10^3$ | 570 | ND | 0 |
| 300 | 10 | 1:30 | 510* | 0*** | ND | 0 |
| 300 | 20 | 1:15 | 250** | 0*** | ND | 0 |
| 300 | 30 | 1:10 | 630* | 0*** | ND | 0 |
| 500 | 0 | — | $9.0 \times 10^3$ | 300 | ND | 0 |
| 500 | 10 | 1:50 | 560** | 0*** | ND | 0 |
| 500 | 20 | 1:25 | 290*** | 0*** | ND | 0 |
| 500 | 30 | 1:16.7 | 620*** | 0*** | ND | 0 |
| | | | Synthetic | | | |
| 0 | 0 | — | $4.2 \times 10^4$ | $2.3 \times 10^4$ | ND | $3.5 \times 10^4$ |
| 0 | 0 | — | $3.5 \times 10^4$ | ND | $3.2 \times 10^4$ | ND |
| 0 | 10 | — | $7.5 \times 10^4$ | $3.1 \times 10^4$ | ND | $1.4 \times 10^4$ |
| 0 | 20 | — | $3.9 \times 10^4$ | $2.2 \times 10^4$ | ND | $1.3 \times 10^4$ |
| 0 | 30 | — | $4.2 \times 10^4$ | $2.1 \times 10^4$ | ND | $5.0 \times 10^3$ |
| 0 | 100 | — | $2.1 \times 10^4$ | ND | $6.0 \times 10^3$ | ND |
| 0 | 500 | — | $9.0 \times 10^3$ | ND | $5.0 \times 10^3$ | ND |
| 0 | 1000 | — | $4.0 \times 10^3$ | ND | $2.0 \times 10^3$ | ND |
| 0 | 5000 | — | $2.0 \times 10^3$ | ND | $4.0 \times 10^3$ | ND |
| 100 | 0 | — | $3.0 \times 10^4$ | $2.0 \times 10^{3}$* | ND | $2.0 \times 10^3$ |
| 100 | 0 | — | $9.0 \times 10^3$ | ND | $5.0 \times 10^3$ | ND |
| 100 | 10 | 1:10 | $3.9 \times 10^4$ | $2.0 \times 10^3$ | ND | 200** |
| 100 | 20 | 1:5 | $2.8 \times 10^4$ | $1.0 \times 10^4$ | ND | 420* |
| 100 | 30 | 1:3.3 | $5.0 \times 10^4$ | $1.0 \times 10^4$ | ND | 0*** |
| 100 | 100 | 1:1 | $7.0 \times 10^{3}$* | ND | 0*** | ND |

TABLE 10b-continued

Efficacy of Various Mixtures of NaPT and Zinc Ions Against Fungi in 5% Metalworking Fluid.

| NaPT PPM | Zn (II) PPM | Ratio Zn:PT | Fungi/ml | | | |
|---|---|---|---|---|---|---|
| | | | Day 1 | Day 2 | Day 4 | Day 7 |
| 100 | 500 | 5:1 | $3.0 \times 10^{3}$* | ND | 0*** | ND |
| 100 | 1000 | 10:1 | $2.1 \times 10^{2}$** | ND | 0*** | ND |
| 100 | 5000 | 50:1 | 0*** | ND | 0*** | ND |
| 300 | 0 | — | $2.9 \times 10^{4}$ | $2.1 \times 10^{4}$ | ND | $1.2 \times 10^{4}$ |
| 300 | 10 | 1:30 | $4.4 \times 10^{4}$* | $1.7 \times 10^{4}$* | ND | 130*** |
| 300 | 20 | 1:15 | $3.2 \times 10^{4}$ | $1.3 \times 10^{4}$* | ND | 370*** |
| 300 | 30 | 1:10 | $7.0 \times 10^{4}$ | $1.4 \times 10^{4}$* | ND | 220*** |
| 500 | 0 | — | $2.7 \times 10^{4}$ | $4.0 \times 10^{3}$ | ND | $3.0 \times 10^{3}$ |
| 500 | 10 | 1:50 | $3.5 \times 10^{4}$* | $1.3 \times 10^{4}$ | ND | 30*** |
| 500 | 20 | 1:25 | $5.2 \times 10^{4}$ | $1.8 \times 10^{4}$ | ND | 40*** |
| 500 | 30 | 1:16.7 | $5.1 \times 10^{4}$ | $1.4 \times 10^{4}$ | ND | 80*** |

ND, not determined

In Tables 10a and 10b, "*" indicates enhanced efficacy for mixture; e.g., efficacy of the mixture of NaPT and Zinc ions is greater than the sum of the efficacies of the corresponding NaPT and Zinc ion controls. "" indicates enhanced efficacy for mixture; e.g., efficacy of the mixture of NaPT and Zinc ions is at least 5-fold greater than the sum of the efficacies of the corresponding NaPT and Zinc ion controls. "*" indicates enhanced efficacy for mixture; e.g., efficacy of the mixture of NaPT and Zinc ions is at least 10-fold greater than the sum of the efficacies of the corresponding NaPT and Zinc ion controls.

As shown in Tables 10a and 10b, initial sampling of tubes demonstrated that all test culture tubes had at least $10^5$ bacteria/ml and $10^4$ fungi/ml before treatment. The different types of metalworking fluids varied in the effects of treatments on the bacteria and fungal contamination present. The microbiocidal efficacy of the controls and treatments was defined as the difference in cells/ml between the treated cultures and the untreated control (e.g. $\log_{10}$ cells/ml untreated–$\log_{10}$ cells/ml treated). Enhancement of efficacy for NaPT and zinc (II) ion mixtures was indicated whenever the efficacy of the mixtures was greater than the sum of the efficacies of the corresponding NaPT and Zinc (II) controls. Results indicate that mixtures of pyrithione and Zinc (II) ions with weight ratios of Zinc(II) ions to pyrithione from 50:1 to 1:50 demonstrated an unexpected enhancement of microbiocidal activity against the bacteria and the fungi in metalworking fluid at some point over the seven days of treatment.

Although the invention has been shown and described with respect to illustrative embodiments thereof, it should be appreciated that the foregoing and various other changes, omissions and additions in the form and detail thereof may be made without departing from the spirit and scope of the invention as delineated in the claims. All patents and patent applications mentioned are herein incorporated by reference in their entirety.

What is claimed is:

1. A method of inhibiting the growth of microorganisms selected from the group consisting of free-living microorganisms, parasitic microorganisms, adherent microorganisms, biofilms, and combinations thereof, characterized by the step of contacting said microorganisms with an antimicrobial composition comprising a pyrithione salt selected from the group consisting of sodium pyrithione, zinc pyrithione, copper pyrithione, and combinations thereof; and a copper source selected from the group consisting of copper salts, copper oxides, copper hydroxides, copper metals, and combinations thereof; wherein the weight ratio of said copper source to said pyrithione salt is in the range from about 1:100 to about 1:1, and wherein said antimicrobial composition has an enhanced biocidal effect against said microorganisms, wherein said copper salt is selected from the group consisting of copper disodium citrate, copper triethanolamine, copper carbonate, cuprous ammonium carbonate, cupric hydroxide, copper chloride, cupric chloride, copper ethylenediamine complex, copper oxychloride, copper oxychloride sulfate, cuprous oxide, copper thiocyanate, and combinations thereof.

2. The method of claim 1, wherein said copper source is generated electrolytically.

3. The method of claim 1, wherein said microorganisms are selected from the group consisting of *Pseudomonas aeruginosa, Aspergillus niger, Fusarim, Cephalosporium, Pseudomonasfluorescens, Pseudomonas rubescens, Pseudomonas stutzeri, Pseudomonas olevorans, Alcaligenes faecalis, Citrobacter freundii, Escherichia coli, Staphylococcus aureus, Candida albicans, Pityrosporum ovale*, and combinations thereof.

4. A fuel, fluid, or lubricant, comprising water or an organic base fluid and an antimicrobial composition, said antimicrobial composition comprising a pyrithione salt selected from the group consisting of sodium pyrithione, zinc pyrithione, copper pyrithione, and combinations thereof; and a copper source selected from the group consisting of copper salts, copper oxides, copper hydroxides, copper metals, and combinations thereof; wherein the weight ratio of said copper source to said pyrithione salt is in the range from about 1:100 to about 1:1, and wherein said antimicrobial composition has an enhanced biocidal effect against microorganisms selected from the group consisting of free-living microorganisms, parasitic microorganisms, adherent microorganisms, bio films, and combinations thereof, and wherein said copper salt is selected from the group consisting of copper disodium citrate, copper triethanolamine, copper carbonate, cuprous ammonium carbonate, cupric hydroxide, copper chloride, cupric chloride, copper ethylenediamine complex, copper oxychloride, copper oxychloride sulfate, cuprous oxide, copper thiocyanate, and combinations thereof.

5. The fuel, fluid, or lubricant of claim 4, further comprising a component selected from the group consisting of corrosion inhibitors, surfactants, and combinations thereof.

6. A method of preserving detergents or surfactants, comprising the steps of:
contacting a detergent or surfactant with an antimicrobial composition, comprising: a pyrithione salt selected from the group consisting of sodium pyrithione, zinc pyrithione, copper pyrithione, and combinations thereof; and a copper source selected from the group consisting of copper salts, copper oxides, copper hydroxides, copper metals, and combinations thereof;

wherein the weight ratio of said copper source to said pyrithione salt is in the range from about 1:100 to 1:1, and wherein said antimicrobial composition has an enhanced biocidal effect against microorganisms selected from the group consisting of free-living microorganisms, parasitic microorganisms, adherent microorganisms, bio films, and combinations thereof, and wherein said copper salt is selected from the group consisting of copper disodium citrate, copper triethanolamine, copper carbonate, cuprous ammonium carbonate, cupric hydroxide, copper chloride, cupric chloride, copper ethylenediamine complex, copper oxychloride, copper oxychloride sulfate, cuprous oxide, copper thiocyanate, and combinations thereof.

7. A pharmaceutical composition, comprising:
(a) a pharmaceutically acceptable carrier; and
(b) an antimicrobial composition, comprising a pyrithione salt selected from the group consisting of sodium pyrithione, zinc pyrithione, copper pyrithione, and combinations thereof; and a copper source selected from the group consisting of copper salts, copper oxides, copper hydroxides, copper metals, and combinations thereof;

wherein the weight ratio of said copper source to said pyrithione salt is in the range from about 1:100 to about 1:1, and wherein said antimicrobial composition has an enhanced biocidal effect against microorganisms selected from the group consisting of free-living microorganisms, parasitic microorganisms, adherent microorganisms, biofilms, and combinations thereof, and wherein said copper salt is selected from the group consisting of copper disodium citrate, copper triethanolamine, copper carbonate, cuprous ammonium carbonate, cupric hydroxide, copper chloride, cupric chloride, copper ethylenediamine complex, copper oxychloride, copper oxychloride sulfate, cuprous oxide, copper thiocyanate, and combinations thereof.

8. A method of inhibiting the growth of microorganisms selected from the group consisting of free-living microorganisms, parasitic microorganisms, adherent microorganisms, biofilms, and combinations thereof, characterized by the step of contacting said microorganisms with an antimicrobial composition comprising a pyrithione salt selected from the group consisting sodium pyrithione, zinc pyrithione, copper pyrithione, and combinations thereof; and a copper source selected from the group consisting of copper salts, copper oxides, copper hydroxides, copper metals, and combinations thereof; wherein the weight ratio of said copper source to said pyrithione salt is in the range from about 1:100 to about 1:1, and wherein said antimicrobial composition has an enhanced biocidal effect against said microorganisms, selected from the group consisting of free-living microorganisms, parasitic microorganisms, adherent microorganisms, bio films, and combinations thereof, said antimicrobial composition additionally comprises alkanolamine, and wherein said copper salt is selected from the group consisting of copper disodium citrate, copper triethanolamine, copper carbonate, cuprous ammonium carbonate, cupric hydroxide, copper chloride, cupric chloride, copper ethylenediamine complex, copper oxychloride, copper oxychloride sulfate, cuprous oxide, copper thiocyanate, and combinations thereof.

9. The method of claim 1 wherein the pyrithione salt is zinc pyrithione.

10. The method of claim 1 wherein the pyrithione salt is sodium pyrithione.

11. The fuel, fluid, or lubricant of claim 4 wherein the pyrithione salt is sodium pyrithione.

* * * * *